US010959664B2

United States Patent
Burns et al.

(10) Patent No.: US 10,959,664 B2
(45) Date of Patent: *Mar. 30, 2021

(54) MEASUREMENT OF SUSCEPTIBILITY TO DIABETIC FOOT ULCERS

(71) Applicant: BBI MEDICAL INNOVATIONS, LLC, Los Angeles, CA (US)

(72) Inventors: Martin F. Burns, Los Angeles, CA (US); Sara Barrington, Thousand Oaks, CA (US); Graham O. Ross, Oceanside, CA (US)

(73) Assignee: BBI Medical Innovations, LLC, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/676,388

(22) Filed: Nov. 6, 2019

(65) Prior Publication Data

US 2020/0069242 A1 Mar. 5, 2020

Related U.S. Application Data

(63) Continuation of application No. 15/887,886, filed on Feb. 2, 2018.

(Continued)

(51) Int. Cl.
*A61B 5/00* (2006.01)
*A61F 13/06* (2006.01)
(Continued)

(52) U.S. Cl.
CPC ............ *A61B 5/447* (2013.01); *A61B 5/0531* (2013.01); *A61B 5/6829* (2013.01);
(Continued)

(58) Field of Classification Search
CPC ....... A61B 5/01; A61B 5/0531; A61B 5/0537; A61B 5/445; A61B 5/447; A61B 5/4878;
(Continued)

(56) References Cited

U.S. PATENT DOCUMENTS 4,857,716 A 8/1989 Gombrich et al.
4,860,753 A 8/1989 Amerena
(Continued)

FOREIGN PATENT DOCUMENTS

CA 2811609 11/2011
CA 2609842 C 10/2016
(Continued)

OTHER PUBLICATIONS

Gershon, S., et al. "SEM Scanner readings to assess pressure induced tissue damage." 17th Annual European Pressure Ulcer Advisory Panel (EPUAP) meeting, Stockholm, Sweden. 2014. (Year: 2014).*
(Continued)

*Primary Examiner* — Jonathan T Kuo
(74) *Attorney, Agent, or Firm* — Arnold & Porter Kaye Scholer LLP

(57) ABSTRACT

The present disclosure provides apparatuses and methods for measuring capacitance as an indication of susceptibility to the formation of a diabetic foot ulcer.

18 Claims, 20 Drawing Sheets

Related U.S. Application Data

(60) Provisional application No. 62/454,482, filed on Feb. 3, 2017, provisional application No. 62/521,917, filed on Jun. 19, 2017.

(51) Int. Cl.
 *A61B 5/0531* (2021.01)
 *A61B 5/0537* (2021.01)
 *G01R 27/26* (2006.01)
 *A61B 5/01* (2006.01)

(52) U.S. Cl.
 CPC .............. *A61F 13/064* (2013.01); *A61B 5/01* (2013.01); *A61B 5/0537* (2013.01); *A61B 5/445* (2013.01); *A61B 5/4878* (2013.01); *G01R 27/2605* (2013.01)

(58) Field of Classification Search
 CPC .. A61B 5/6829; A61F 13/064; G01R 27/2605
 See application file for complete search history.

(56) References Cited

U.S. PATENT DOCUMENTS

| | | | |
|---|---|---|---|
| 5,073,126 | A | 12/1991 | Kikuchi et al. |
| 5,284,150 | A | 2/1994 | Butterfield et al. |
| 5,367,789 | A | 11/1994 | Lamont |
| 5,904,581 | A | 5/1999 | Pope et al. |
| 6,330,479 | B1 | 12/2001 | Stauffer |
| 6,370,426 | B1 | 4/2002 | Campbell et al. |
| 6,434,422 | B1 | 8/2002 | Tomoda et al. |
| 6,577,700 | B1 | 6/2003 | Fan et al. |
| 6,634,045 | B1 | 10/2003 | DuDonis et al. |
| 6,738,798 | B1 | 5/2004 | Ploetz et al. |
| 6,963,772 | B2 | 11/2005 | Bloom et al. |
| 7,079,899 | B2 | 7/2006 | Petrofsky |
| 7,315,767 | B2 | 1/2008 | Caduff et al. |
| 7,402,135 | B2 | 7/2008 | Leveque et al. |
| 7,783,344 | B2 | 8/2010 | Lackey et al. |
| 8,011,041 | B2 | 9/2011 | Hann |
| 8,355,925 | B2 | 1/2013 | Rothman et al. |
| 8,390,583 | B2 | 3/2013 | Forutanpour et al. |
| 8,925,392 | B2 | 1/2015 | Esposito et al. |
| 9,028,407 | B1 | 5/2015 | Bennett-Guerrero |
| 9,095,305 | B2 * | 8/2015 | Engler ................... A61B 5/447 |
| 9,220,455 | B2 | 12/2015 | Sarrafzadeh et al. |
| 9,271,676 | B2 | 3/2016 | Alanen et al. |
| 9,398,879 | B2 | 7/2016 | Sarrafzadeh et al. |
| 9,675,289 | B2 | 6/2017 | Heaton |
| 9,763,596 | B2 | 9/2017 | Tonar et al. |
| 9,949,683 | B2 | 4/2018 | Afentakis |
| 9,980,673 | B2 | 5/2018 | Sarrafzadeh et al. |
| 10,085,643 | B2 | 10/2018 | Bandic et al. |
| 10,166,387 | B2 | 1/2019 | Bergelin et al. |
| 10,178,961 | B2 | 1/2019 | Tonar et al. |
| 10,182,740 | B2 | 1/2019 | Tonar et al. |
| 10,188,340 | B2 | 1/2019 | Sarrafzadeh et al. |
| 10,194,856 | B2 | 2/2019 | Afentakis et al. |
| 10,206,604 | B2 | 2/2019 | Bergelin et al. |
| 10,226,187 | B2 | 3/2019 | Al-Ali et al. |
| 10,285,898 | B2 | 5/2019 | Douglas et al. |
| 10,307,060 | B2 | 6/2019 | Tran |
| 10,342,482 | B1 | 7/2019 | Lisy et al. |
| 10,383,527 | B2 | 8/2019 | Al-Ali |
| 10,420,602 | B2 | 9/2019 | Horton et al. |
| 10,441,185 | B2 | 10/2019 | Rogers et al. |
| 10,448,844 | B2 | 10/2019 | Al-Ali et al. |
| 10,463,293 | B2 | 11/2019 | Maharbiz et al. |
| 10,485,447 | B2 | 11/2019 | Tonar et al. |
| 2001/0051783 | A1 | 12/2001 | Edwards et al. |
| 2002/0016535 | A1 | 2/2002 | Martin et al. |
| 2002/0070866 | A1 | 6/2002 | Newham |
| 2002/0143262 | A1 | 10/2002 | Bardy |
| 2003/0036674 | A1 | 2/2003 | Bouton |
| 2003/0036713 | A1 | 2/2003 | Bouton et al. |
| 2003/0110662 | A1 | 6/2003 | Gilman et al. |
| 2003/0116447 | A1 | 6/2003 | Surridge et al. |
| 2003/0139255 | A1 | 7/2003 | Lina |
| 2004/0046668 | A1 | 3/2004 | Smith et al. |
| 2004/0054298 | A1 | 3/2004 | Masuo et al. |
| 2004/0080325 | A1 | 4/2004 | Ogura |
| 2004/0133092 | A1 | 7/2004 | Kain |
| 2004/0171962 | A1 | 9/2004 | Leveque et al. |
| 2004/0176754 | A1 | 9/2004 | Island et al. |
| 2004/0236200 | A1 | 11/2004 | Say et al. |
| 2004/0254457 | A1 | 12/2004 | Van Der Weide |
| 2005/0027175 | A1 | 2/2005 | Yang |
| 2005/0070778 | A1 | 3/2005 | Lackey et al. |
| 2005/0096513 | A1 | 5/2005 | Ozguz et al. |
| 2005/0177061 | A1 | 8/2005 | Alanen et al. |
| 2005/0203435 | A1 | 9/2005 | Nakada |
| 2005/0215918 | A1 | 9/2005 | Frantz et al. |
| 2005/0245795 | A1 | 11/2005 | Goode et al. |
| 2005/0251418 | A1 | 11/2005 | Fox, Jr. et al. |
| 2006/0058593 | A1 | 3/2006 | Drinan et al. |
| 2006/0097949 | A1 | 5/2006 | Luebke et al. |
| 2006/0206013 | A1 | 9/2006 | Rothman et al. |
| 2007/0106172 | A1 | 5/2007 | Abreu |
| 2007/0179585 | A1 * | 8/2007 | Chandler ............. A61N 1/0468 623/1.1 |
| 2007/0191273 | A1 | 8/2007 | Ambati et al. |
| 2008/0009764 | A1 | 1/2008 | Davies |
| 2008/0015894 | A1 | 1/2008 | Miller et al. |
| 2008/0259577 | A1 | 10/2008 | Hu et al. |
| 2008/0278336 | A1 | 11/2008 | Ortega et al. |
| 2009/0124924 | A1 | 5/2009 | Eror et al. |
| 2009/0189092 | A1 | 7/2009 | Aoi et al. |
| 2010/0017182 | A1 | 1/2010 | Voros et al. |
| 2010/0113979 | A1 | 5/2010 | Sarrafzadeh et al. |
| 2010/0298687 | A1 | 11/2010 | Yoo et al. |
| 2010/0324611 | A1 * | 12/2010 | Deming ............... A43B 3/0005 607/2 |
| 2011/0184264 | A1 | 7/2011 | Galasso, Jr. et al. |
| 2011/0191122 | A1 | 8/2011 | Kharraz Tavakol et al. |
| 2011/0263950 | A1 | 10/2011 | Larson et al. |
| 2011/0301441 | A1 | 12/2011 | Bandic et al. |
| 2011/0313311 | A1 | 12/2011 | Gaw |
| 2012/0029410 | A1 | 2/2012 | Koenig et al. |
| 2012/0061257 | A1 | 3/2012 | Yu et al. |
| 2012/0078088 | A1 | 3/2012 | Whitestone et al. |
| 2012/0150011 | A1 | 6/2012 | Besio |
| 2012/0190989 | A1 | 7/2012 | Kaiser et al. |
| 2012/0271121 | A1 | 10/2012 | Della Torre et al. |
| 2013/0041235 | A1 | 2/2013 | Rogers et al. |
| 2013/0121544 | A1 | 5/2013 | Sarrafzadeh et al. |
| 2013/0123587 | A1 | 5/2013 | Sarrafzadeh et al. |
| 2013/0137951 | A1 | 5/2013 | Chuang et al. |
| 2013/0253285 | A1 | 9/2013 | Bly et al. |
| 2013/0261496 | A1 * | 10/2013 | Engler ................... A61B 5/447 600/549 |
| 2013/0310440 | A1 | 11/2013 | Duskin et al. |
| 2013/0333094 | A1 | 12/2013 | Rogers et al. |
| 2013/0338661 | A1 | 12/2013 | Behnke, II |
| 2014/0121479 | A1 | 5/2014 | O'Connor et al. |
| 2014/0142984 | A1 | 5/2014 | Wright et al. |
| 2014/0288397 | A1 | 6/2014 | Sarrafzadeh et al. |
| 2014/0200486 | A1 | 7/2014 | Bechtel et al. |
| 2014/0275823 | A1 | 9/2014 | Lane et al. |
| 2014/0316297 | A1 | 10/2014 | McCaughan et al. |
| 2015/0002168 | A1 | 1/2015 | Kao et al. |
| 2015/0094548 | A1 | 4/2015 | Sabatini et al. |
| 2015/0230863 | A1 | 8/2015 | Youngquist et al. |
| 2015/0363567 | A1 | 12/2015 | Pettus |
| 2015/0366499 | A1 * | 12/2015 | Sarrafzadeh ........... A61B 5/445 600/306 |
| 2016/0101282 | A1 | 4/2016 | Bergelin et al. |
| 2016/0174871 | A1 | 6/2016 | Sarrafzadeh et al. |
| 2016/0220172 | A1 | 8/2016 | Sarrafzadeh et al. |
| 2016/0270968 | A1 | 9/2016 | Stanford et al. |
| 2016/0278692 | A1 | 9/2016 | Larson et al. |
| 2016/0296268 | A1 | 10/2016 | Gee et al. |
| 2016/0310034 | A1 | 10/2016 | Tonar et al. |
| 2016/0338591 | A1 | 11/2016 | Lachenbruch et al. |
| 2017/0007153 | A1 | 1/2017 | Tonar et al. |

(56) References Cited

U.S. PATENT DOCUMENTS

| | | | |
|---|---|---|---|
| 2017/0014044 A1 | 1/2017 | Tonar et al. | |
| 2017/0014045 A1 | 1/2017 | Tonar et al. | |
| 2017/0156658 A1 | 6/2017 | Maharbiz et al. | |
| 2017/0172489 A1 | 6/2017 | Afentakis | |
| 2017/0188841 A1 | 7/2017 | Ma et al. | |
| 2017/0311807 A1 | 11/2017 | Fu et al. | |
| 2018/0220924 A1 | 8/2018 | Burns et al. | |
| 2018/0220953 A1 | 8/2018 | Burns et al. | |
| 2018/0220954 A1* | 8/2018 | Burns | A61B 5/6829 |
| 2018/0220961 A1 | 8/2018 | Burns et al. | |
| 2018/0360344 A1 | 12/2018 | Burns et al. | |
| 2019/0000352 A1 | 1/2019 | Everett et al. | |
| 2019/0038133 A1 | 2/2019 | Tran | |
| 2019/0060602 A1 | 2/2019 | Tran et al. | |
| 2019/0104981 A1 | 4/2019 | Sarrafzadeh et al. | |
| 2019/0104982 A1 | 4/2019 | Dunn et al. | |
| 2019/0134396 A1 | 5/2019 | Toth et al. | |
| 2019/0142333 A1 | 5/2019 | Burns et al. | |
| 2019/0147990 A1 | 5/2019 | Burns et al. | |
| 2019/0150882 A1 | 5/2019 | Maharbiz et al. | |
| 2019/0175098 A1 | 6/2019 | Burns et al. | |
| 2019/0192066 A1 | 6/2019 | Schoess et al. | |
| 2019/0246972 A1 | 8/2019 | Burns et al. | |
| 2019/0282436 A1 | 9/2019 | Douglas et al. | |
| 2019/0290189 A1 | 9/2019 | Sarrafzadeh et al. | |
| 2019/0307360 A1 | 10/2019 | Tonar et al. | |
| 2019/0307405 A1 | 10/2019 | Terry et al. | |
| 2020/0069240 A1 | 3/2020 | Burns | |
| 2020/0069241 A1 | 3/2020 | Burns | |
| 2020/0077892 A1 | 3/2020 | Tran | |
| 2020/0078499 A1 | 3/2020 | Gadde et al. | |
| 2020/0093395 A1 | 3/2020 | Tonar et al. | |
| 2020/0100723 A1 | 4/2020 | Burns | |
| 2020/0113488 A1 | 4/2020 | Al-Ali et al. | |
| 2020/0127398 A1 | 4/2020 | Burns et al. | |
| 2020/0297244 A1 | 9/2020 | Brownhill et al. | |
| 2020/0297255 A1 | 9/2020 | Martinez et al. | |

FOREIGN PATENT DOCUMENTS

| | | |
|---|---|---|
| EP | 1080687 A1 | 3/2001 |
| EP | 1372475 B1 | 1/2004 |
| EP | 1569553 A1 | 9/2005 |
| EP | 3092946 A1 | 11/2016 |
| EP | 3280488 B1 | 12/2018 |
| JP | 2003-169788 A | 6/2003 |
| JP | 2003-290166 A | 10/2003 |
| JP | 2005-52227 | 3/2005 |
| JP | 4418419 | 2/2010 |
| JP | 2013-528428 | 7/2013 |
| JP | 2013-198639 A | 10/2013 |
| JP | 2015-509028 | 3/2015 |
| JP | 2016-519969 | 7/2016 |
| JP | 2016-527943 A | 9/2016 |
| KR | 10-2014-0058445 | 5/2014 |
| WO | 96/10951 A1 | 4/1996 |
| WO | 2002/080770 A1 | 10/2002 |
| WO | 2004/105602 A1 | 12/2004 |
| WO | 2006/029035 A1 | 3/2006 |
| WO | 2007/098762 A1 | 9/2007 |
| WO | 2009/144615 A1 | 12/2009 |
| WO | 2011/022418 A2 | 2/2011 |
| WO | 2011/143071 A2 | 11/2011 |
| WO | 2013/116242 A2 | 8/2013 |
| WO | 2014/186894 A1 | 11/2014 |
| WO | 2015/003015 A2 | 1/2015 |
| WO | 2015/168720 A1 | 11/2015 |
| WO | 2015/169911 A1 | 11/2015 |
| WO | 2015/195720 A1 | 12/2015 |
| WO | 2016/172263 A1 | 10/2016 |
| WO | 2016/172264 A1 | 10/2016 |
| WO | 2017/032393 | 3/2017 |
| WO | 2017/214188 A1 | 12/2017 |
| WO | 2018/071715 A1 | 4/2018 |
| WO | 2018/115461 A1 | 6/2018 |
| WO | 2018/144938 | 8/2018 |
| WO | 2018/144941 | 8/2018 |
| WO | 2018/144943 | 8/2018 |
| WO | 2018/144946 | 8/2018 |
| WO | 2018/189265 A1 | 10/2018 |
| WO | 2018/209100 A1 | 11/2018 |
| WO | 2018/234443 A1 | 12/2018 |
| WO | 2018/236739 | 12/2018 |
| WO | 2019/020551 A1 | 1/2019 |
| WO | 2019/030384 A2 | 2/2019 |
| WO | 2019/048624 A1 | 3/2019 |
| WO | 2019/048626 A1 | 3/2019 |
| WO | 2019/048638 A1 | 3/2019 |
| WO | 2019/072531 A1 | 4/2019 |
| WO | 2019/073389 A1 | 4/2019 |
| WO | 2019/076967 A2 | 4/2019 |
| WO | 2019/096828 A1 | 5/2019 |
| WO | 2019/099810 | 5/2019 |
| WO | 2019/099812 A1 | 5/2019 |
| WO | 2019/113481 | 6/2019 |
| WO | 2019/157290 | 8/2019 |
| WO | 2020/014779 A1 | 1/2020 |
| WO | 2020/077100 A1 | 4/2020 |
| WO | 2020/043806 A1 | 5/2020 |

OTHER PUBLICATIONS

Moore Z, Gershon S, Fletcher J. SEM Scanner Made Easy. Wounds International 2018; Available at: www.woundsinternational.com (Year: 2018).*

Zanibbi, Pattern Recognition: An Overview; 2010; https://www.cs.rit.edu/~rlaz/prec20092/slides/Overview.pdf (Year: 2010).*

Alanen, "Measurement of Hydration in the Stratum Corneum with the MoistureMeter and Comparison with the Corneometer," *Skin Research and Technology*, 10:32-37 (2004).

Alberts et al., "The Extracellular Matrix of Animals," *Molecular Biology of the Cell*, 4th ed., pp. 1065-1127 (2002).

Allman et al., "Pressure Ulcer Risk Factors Among Hospitalized Patients with Activity Limitation," *JAMA*, 273:865-870 (1995).

Anonymous, "Recommended Practices for Positioning the Patient in the Perioperative Practice Setting," in *Perioperative Standards, Recommended Practices, and Guidelines*, AORN, Inc., 525-548 (2006).

Arao et al., "Morphological Characteristics of the Dermal Papillae in the Development of Pressure Sores," *World Wide Wounds*, (1999).

Australian Intellectual Property Office, Office Action dated May 1, 2014 for corresponding Australian patent application No. 2011253253 (pp. 1-10) and pending claims (pp. 11-15) pp. 1-15.

Australian Patent Office, Office Action dated Jun. 1, 2015, for corresponding Australian Patent Application No. 2011253253 (pp. 1-4) and claims (pp. 5-10) pp. 1-10.

Bader et al., "Effect of Externally Applied Skin Surface Forces on Tissue Vasculature," *Archives of Physical Medicine and Rehabilitation*, 67(11):807-11 (1986).

Barnes, "Moisture Meters for Use on Thin Lumber and Veneers," *Moisture Register Co.*, 1-5 (1956).

Bates-Jensen et al., "Subepidermal Moisture Predicts Erythema and Stage 1 Pressure Ulcers in Nursing Home Residents: A Pilot Study," *Journal of the American Geriatric Society*, 55:1199-1205 (2007).

Bates-Jensen et al., "Subepidermal moisture differentiates erythema and stage 1 pressure ulcers in nursing home residents," *Wound Repair Regeneration*, 16:189-197 (2008).

Bates-Jensen et al., "Subepidermal Moisture Is Associated With Early Pressure Ulcer Damage in Nursing Home Residents With Dark Skin Tones; Pilot Findings," *Journal of Wound Ostomy and Continence Nursing*, 36(3):277-284 (2009).

Bergstrand et al., "Pressure-induced Vasodilation and Reactive Hyperemia at Different Depths in Sacral Tissue Under Clinically Relevant Conditions," *Microcirculation*, 21:761-771 (2014).

Bergstrom et al., "Pressure Ulcers in Adults: Prediction and Prevention," *Clinical Practice Guideline—Quick Reference Guide for Clinicians*, 117 (1992).

(56) References Cited

OTHER PUBLICATIONS

Brem et al. "High cost of stage IV pressure ulcers," *American Journal of Surgery*, 200:473-477 (2010).
Brienza et al., "Friction-Induced Skin Injuries—Are They Pressure Ulcers?," *Journal of Wound Ostomy and Continence Nursing*, 42(1):62-64 (2015).
Carmo-Araujo et al., "Ischaemia and reperfusion effects on skeletal muscle tissue: morphological and histochemical studies," *International Journal of Experimental Pathology*, 88:147-154 (2007).
Ceelen et al., "Compression-induced damage and internal tissue strains are related," *Journal of Biomechanics*, 41:3399-3404 (2008).
Ching et al., "Tissue electrical properties monitoring for the prevention of pressure sore," *Prosthetics and Orthotics International*, 35(4):386-394 (2011).
Clendenin et al., "Inter-operator and inter-device agreement and reliability of the SEM Scanner," *Journal of Tissue Viability*, 24(1):17-23 (2015).
De Lorenzo et al., "Predicting body cell mass with bioimpedance by using theoretical methods: a technological review," *Journal of Applied Physiology*, 82(5):1542-1558 (1997).
Demarre et al., "The cost of pressure ulcer prevention and treatment in hospitals and nursing homes in Flanders: A cost-of-illness study," *International Journal of Nursing Studies*, 1-14 (2015).
Dodde et al., "Bioimpedance of soft tissue under compression," *Physiology Measurement*, 33(6):1095-1109 (2012).
DuPont, "General Specifications for Kapton Polyimide Film," Retrieved from Dupont: http://www2.dupont.com/Kapton/en_US/assets/downloads/pdf/Gen_Specs.pdf, pp. 1-7 (2012).
Dupont, "Pyralux® FR Coverlay, Bondply & Sheet Adhesive," webpage, Retrieved from: www2.dupont.com/Pyralux/en_US/products/adhesives_films/FR/FR_films_html pp. 1-2 (2012).
DuPont, "Pyralux® FR Copper-clad Laminate," webpage, Retrieved from: www2.dupont.com/Pyraluxlen_US/ productsllaminate/FR/pyralux_fr.html, pp. 1-2 (2012).
Eberlein-Gonska et al., "The Incidence and Determinants of Decubitus Ulcers in Hospital Care: An Analysis of Routine Quality Management Data at a University Hospital," *Deutsches Arzteblatt International*, 110(33-34):550-556 (2013).
European Patent Office, ESSR dated Aug. 22, 2014 for corresponding in European Patent Application No. 117811061.4 (pp. 1-7) and pending claims (pp. 3-10) pp. 1-10.
European Patent Office, Office Action dated Jul. 13, 2015, for corresponding European Patent Application No. 11781061.4 (pp. 1-5) and claims (pp. 6-9) pp. 1-9.
Extended European Search Report dated Aug. 19, 2016, in European Patent Application No. 16169670.
Extended European Search Report dated Sep. 19, 2016, in European Patent Application No. 16166483.4.
Extended European Search Report dated Mar. 13, 2017, in European Patent Application No. 16196899.5.
Gabriel, "Compilation of the Dielectric Properties of Body Tissues at RF and Microwave Frequencies Report," *Occupational and Environmental Health Directorate*, (1996).
Gabriel et al., "The dielectric properties of biological tissues: II. Measurements in the frequency range 10 Hz to 20 GHz," *Physics in Medicine and Biology*, 41:2251-69 (1996).
Gardiner et al., "Incidence of hospital-acquired pressure ulcers—a population-based cohort study," *International Wound Journal*, 11(6):696-700 (2014).
Gershon et al., "SEM Scanner Readings to Assess Pressure Induced Tissue Damage," Proceedings of the 17th Annual European Pressure Ulcer Advisory in Panel (EPUAP) meeting, Stockholm, Sweden (2014).
Gonzalez-Correa et al., "Electrical bioimpedance readings increase with higher pressure applied to the measuring probe," *Physiology Measurement*, 26:S39-S47 (2005).
Guihan et al., "Assessing the feasibility of subepidermal moisture to predict erythema and stage 1 pressure ulcers in persons with spinal cord injury: A pilot study," *Journal of Spinal Cord Medicine*, 35(1):46-52 (2012).

Harrow, "Subepidermal moisture surrounding pressure ulcers in persons with a spinal cord injury: A pilot study," *Journal of Spinal Cord Medicine*, 37(6):719-728 (2014).
Houwing et al., "Pressure-induced skin lesions in pigs: reperfusion injury and the effects of vitamin E," *Journal of Wound Care*, 9(1):36-40 (2000).
Huang et al., "A device for skin moisture and environment humidity detection," *Sensors and Actuators B: Chemical*, 206-212 (2008).
International Search Report dated Apr. 12, 2018, issued in International Patent Application No. PCT/US2018/016731.
International Search Report dated Apr. 12, 2018, issued in International Patent Application No. PCT/US2018/016738.
International Search Report dated Apr. 26, 2018, issued in International Patent Application No. PCT/US2018/016741.
International Search Report dated Jul. 12, 2018, issued in International Patent Application No. PCT/US2018/016736.
International Search Report dated Sep. 10, 2018, issued in International Patent Application No. PCT/US2018/038055.
International Search Report dated Jan. 29, 2019, issued in International Patent Application No. PCT/US2018/061494.
International Search Report dated Feb. 5, 2019, issued in International Patent Application No. PCT/US2018/064527.
International Search Report dated Feb. 11, 2019, issued in International Patent Application No. PCT/US2018/061497.
International Search Report dated May 29, 2019, issued in International Patent Application No. PCT/US2019/017226.
International Search Report and Written Opinion dated Feb. 9, 2012 for International Patent Application No. PCT/US2011/035618.
International Search Report and Written Opinion dated Jul. 22, 2016, for International Patent Application No. PCT/US2016/28515.
International Search Report and Written Opinion dated Jul. 26, 2016, for International Patent Application No. PCT/US2016/28516.
Jan et al., "Local cooling reduces skin ischemia under surface pressure in rats: an assessment by wavelet analysis of laser Doppler blood flow oscillations," *Physiology Measurement*, 33(10):1733-1745 (2012).
Jaskowski, "Evaluation of the Healing Process of Skin Wounds by Means of Skin Absolute Value of Electrical Impedance," *Dermatol. Mon.schr.*, 172(4):223-228 (1986).
Jiang et al., "Expression of cytokines, growth factors and apoptosis-related signal molecules in chronic pressure ulcer wounds healing," *Spinal Cord*, 52(2):145-151 (2014).
Jiang et al., "Ischemia-Reperfusion Injury-Induced Histological Changes Affecting Early Stage Pressure Ulcer Development in a Rat model," *Ostomy Wound Management*, 57:55-60 (2011).
Jiricka et al., "Pressure Ulcer Risk factors in an ICU Population," *American Journal of Critical Care*, 4:361-367 (1995).
Kanai et al., "Electrical measurement of fluid distribution in legs and arms," *Medical Progress through Technology Journal*, 12:159-170 (1987).
Kasuya et al., "Potential application of in vivo imaging of impaired lymphatic duct to evaluate the severity of pressure ulcer in mouse model," *Scientific Reports*, 4:4173 (7 pages) (2014).
Lee, "CapSense Best Practices," *Application Note 2394*, 1-10 (2007).
Loerakker et al., "The effects of deformation, ischemia, and reperfusion on the development of muscle damage during prolonged loading," *Journal of Applied Physiology*, 111(4):1168-1177 (2011).
Loerakker et al., "Temporal Effects of Mechanical Loading on Deformation-Induced Damage in Skeletal Muscle Tissue," *Annual Review of Biomedical Engineering*, 38(8):2577-2587 (2010).
Lyder et al., "Quality of Care for Hospitalized Medicare Patients at Risk for Pressure Ulcers," *Archives of Internal Medicine*, 161:1549-1554 (2001).
Martinsen, "Bioimpedance and Bioelectricity Basics," *Elsevier Academic Press*, Chapters 1 and 10 (2015).
Mathiesen et al., "Are labour-intensive efforts to prevent pressure ulcers cost-effective?" *Journal of Medical Economics*, 16(10):1238-1245 (2013).
Matthie et al., "Analytic assessment of the various bioimpedance methods used to estimate body water," *Journal of Applied Physiology*, 84(5):1801-1816 (1998).

(56) References Cited

OTHER PUBLICATIONS

Miller et al., "Lymphatic Clearance during Compressive Loading," *Lymphology*, 14(4):161-166 (1981).
Moore et al., "A randomised controlled clinical trial of repositioning, using the 30° tilt, for the prevention of pressure ulcers," *Journal of Clinical Nursing*, 20:2633-2644 (2011).
Moore et al., "Pressure ulcer prevalence and prevention practices in care of the older person in the Republic of Ireland," *Journal of Clinical Nursing*, 21:362-371 (2012).
Moore et al., "A review of PU prevalence and incidence across Scandinavia, Iceland and Ireland (Part I)", *Journal of Wound Care*, 22(7):361-362, 364-368 (2013).
Mulasi, "Bioimpedance at the Bedside: Current Applications, Limitations, and Opportunities," *Nutritional Clinical Practice*, 30(2):180-193 (2015).
National Pressure Ulcer Advisory Panel et al., "Prevention and Treatment of Pressure Ulcers: Clinical Practice Guideline," *Cambridge Media*, (2014).
Nixon et al., "Pathology, diagnosis, and classification of pressure ulcers: comparing clinical and imaging techniques," *Wound Repair and Regeneration*, 13(4):365-372 (2005).
Nuutinen et al., "Validation of a new dielectric device to asses changes of tissue water in skin and subcutaneous fat," *Physiological Measurement*, 25:447-454 (2004).
O' Goshi, "Skin conductance; validation of Skicon-200EX compared to the original model, Skicon-100," *Skin Research and Technology*, 13:13-18 (2007).
Oomens et al., "Pressure Induced Deep Tissue Injury Explained," *Annual Review of Biomedical Engineering*, 43(2):297-305 (2015).
Scallan et al., "Chapter 4: Pathophysiology of Edema Formation," *Capillary Fluid Exchange: Regulation, Functions, and Pathology*, 47-61 (2010).
Schultz et al., "Extracellular matrix: review of its role in acute and chronic wounds," *World Wide Wounds*, 1-20 (2005).
Schwan, "Electrical properties of tissues and cells," *Advances in Biology and Medical Physics*, 15:148-199 (1957).
Sener et al., "Pressure ulcer-induced oxidative organ injury is ameliorated by beta-glucan treatment in rats," *International Immunopharmacology*, 6(5):724-732 (2006).
Sewchuck et al., "Prevention and Early Detection of Pressure Ulcers in Patients Undergoing Cardiac Surgery," *AORN Journal*, 84(1):75-96 (2006).
Sprigle et al., "Analysis of Localized Erythema Using Clinical Indicators and Spectroscopy,"*Ostomy Wound Management*, 49:42-52 (2003).
Stekelenburg et al., "Deep Tissue Injury: How Deep is Our Understanding?" *Archives of Physical Medicine Rehabilitation*, 89(7):1410-1413 (2008).
Stekelenburg et al., "Role of ischemia and deformation in the onset of compression-induced deep tissue injury: MRI-based studies in a rat model," *Journal of Applied Physiology*, 102:2002-2011 (2007).
Swisher et al., "Impedance sensing device enables early detection of pressure ulcers in vivo," *Nature Communications*, 6:6575-6584 (2015).
Thomas et al., "Hospital-Acquired Pressure Ulcers and Risk of Death," *Journal of the American Geriatrics Society*, 44:1435-1440 (1996).
Valentinuzzi et al., "Bioelectrical Impedance Techniques in Medicine. Part II: Monitoring of Physiological Events by Impedance," *Critical Reviews in Biomedical Engineering*, 24(4-6):353-466 (1996).

Vangilder et al., "Results of Nine International Pressure Ulcer Prevalence Surveys: 1989 to 2005," *Ostomy Wound Management*, 54(2):40-54 (2008).
Wagner et al., "Bioelectrical Impedance as a Discriminator of Pressure Ulcer Risk," *Advances in Wound Care*, 9(2):30-37 (1996).
Wang, "Biomedical System for Monitoring Pressure Ulcer Development" UCLA Electronic Theses and Dissertations, California, USA, pp. 1-123 (2013).
Watanabe et al., "CT analysis of the use of the electrical impedance technique to estimate local oedema in the extremities in patients with lymphatic obstruction," *Medical and Biological Engineering and Computing*, 36(1):60-65 (1998).
Weiss, "Tissue destruction by neutrophils," *The New England Journal of Medicine*, 320(6):365-76 (1989).
Brem et al., "Protocol for the Successful Treatment of Pressure Ulcers," *The American Journal of Surgery*, 188 (Suppl. To Jul. 2004):95-17S (2004).
Extended European Search Report dated Oct. 11, 2019, in European Patent Application No. 19186393.5.
Liu et al., "A Systematic Review of Electrical Stimulation for Pressure Ulcer Prevention and Treatment in People with Spinal Cord Injuries," *The Journal of Spinal Cord Medicine*, 37(6):703-718 (2014).
Rotam et al., "Friction between Human Skin and Medical Textiles for Decubitus Prevention," *Tribology International*, 65:91-96 (2013).
Supplementary Partial European Search Report dated Jan. 27, 2020, issued in EP Application 18747707.
Thomas, "Prevention and Treatment of Pressure Ulcers," *Journal of American Medical Directors Association*, 7(1):46-59 (2006).
Truong et al., "Pressure Ulcer Prevention in the Hospital Setting Using Silicone Foam Dressings," *Cureus*, 8(8):e730, pp. 1-6 (2016).
Tur et al., "Topical Hydrogen Peroxide Treatment of Ischemic Ulcers in the Guinea Pig: Blood Recruitment in Multiple Skin Sites," *Journal of the American Academy of Dermatology*, 33:217-221 (1995).
Extended European Search Report dated Feb. 6, 2020, in European Patent Application No. 18748733.5.
Ford, "Hospice Wins Award for Innovation in Pressure Ulcer Prevention," *Nursing Times*, downloaded and printed on Apr. 18, 2020, from https://www.nursingtimes.net/news/research-and-innovation/hospice-wins-award-for-innovation-in-pressure-ulcer-prevention-30/11/2018/ (2018).
Great Britain Search Report dated Apr. 27, 2020, in Great Britain Patente Application No. GB2002889.0.
International Search Report dated Mar. 9, 2020, issued in International Patent Application No. PCT/US2019/055655.
Seibert et al., "Technical Expert Panel Summary Report: Refinement of a Cross-Setting Pressure Ulcer/Injury Quality Measure for Skilled Nursing Facilities, Inpatient Rehabilitation Facilities, Long-Term Care Hospitals, and Home Health Agencies," RTI International Abt Associates, CMS Contract No. HHSM-500-2013-130151, 49 pp. (Aug. 2019).
Extended European Search Report dated Feb. 10, 2020, in European Patent Application No. 18748512.3.
Extended European Search Report dated Jun. 24, 2020, in European Patent Application No. 18747707.0.
Vowden et al., "Diabetic Foot Ulcer or Pressure Ulcer? That Is the Question," *The Diabetic Foot Journal*, 18:62-66 (2015).
Wang et al., "A Wireless Biomedical Instrument for Evidence-Based Tissue Wound Characterization," *Wireless Health*, pp. 222-223 (2010).

\* cited by examiner

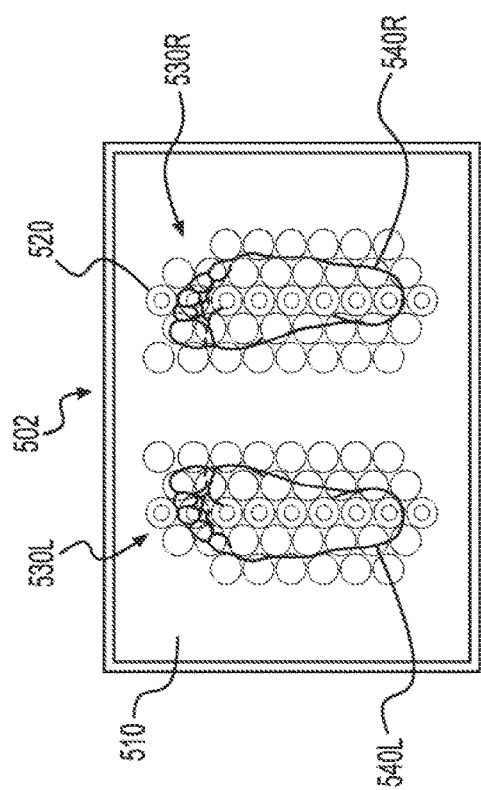
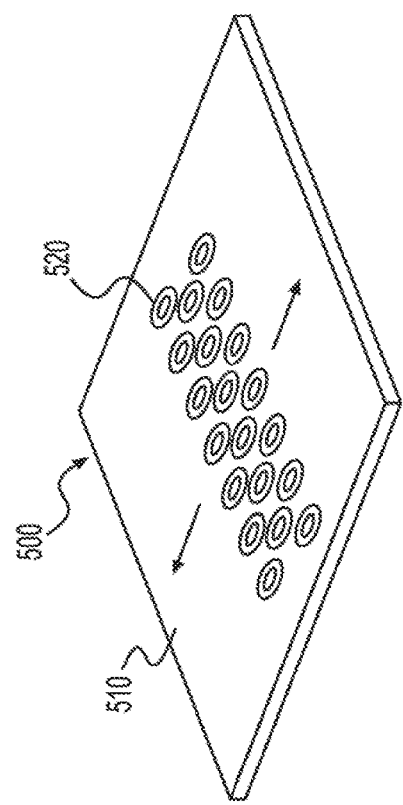
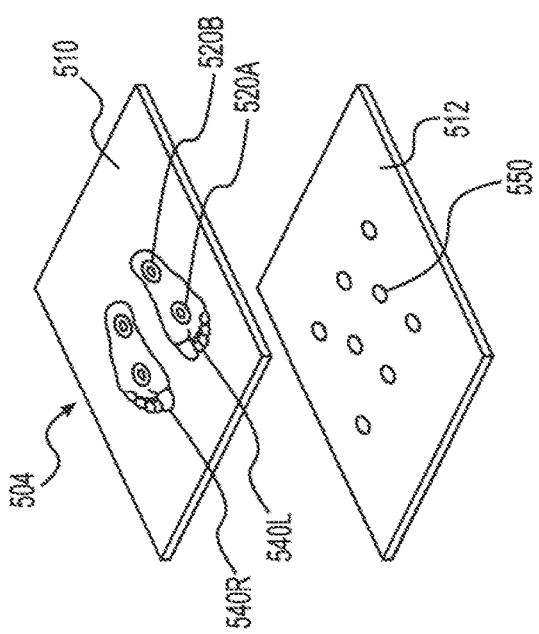
FIG. 7A
FIG. 7B
FIG. 7C

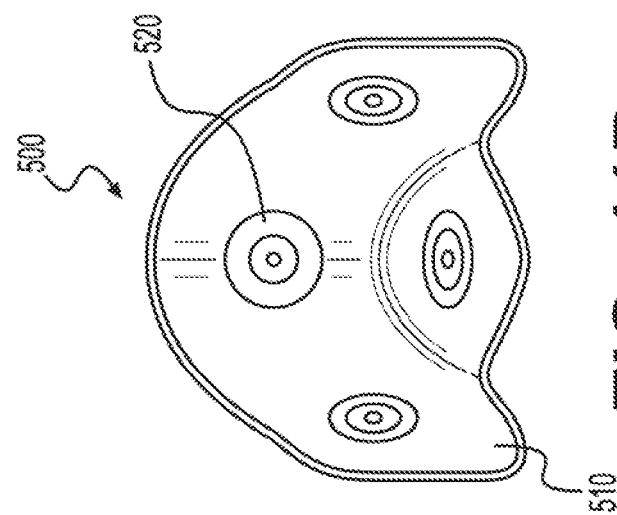
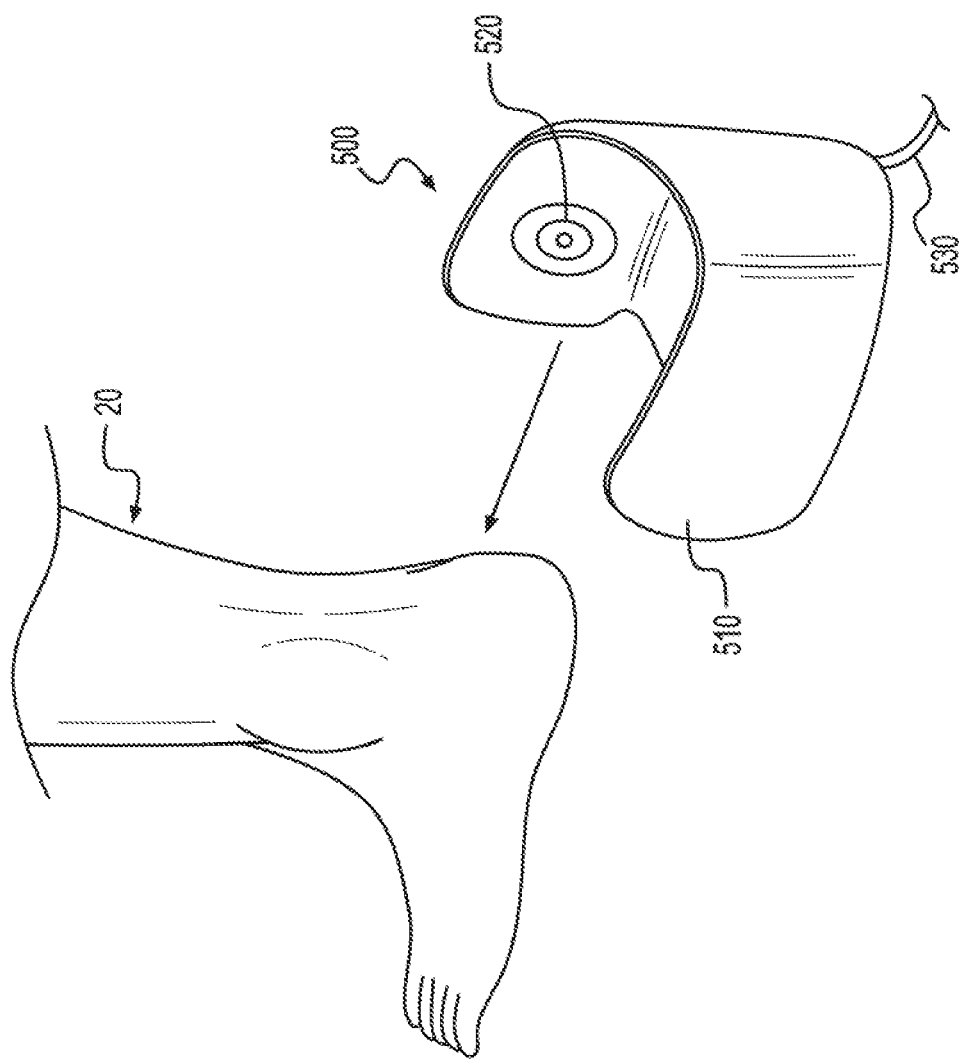
*FIG. 11B*
*FIG. 11A*

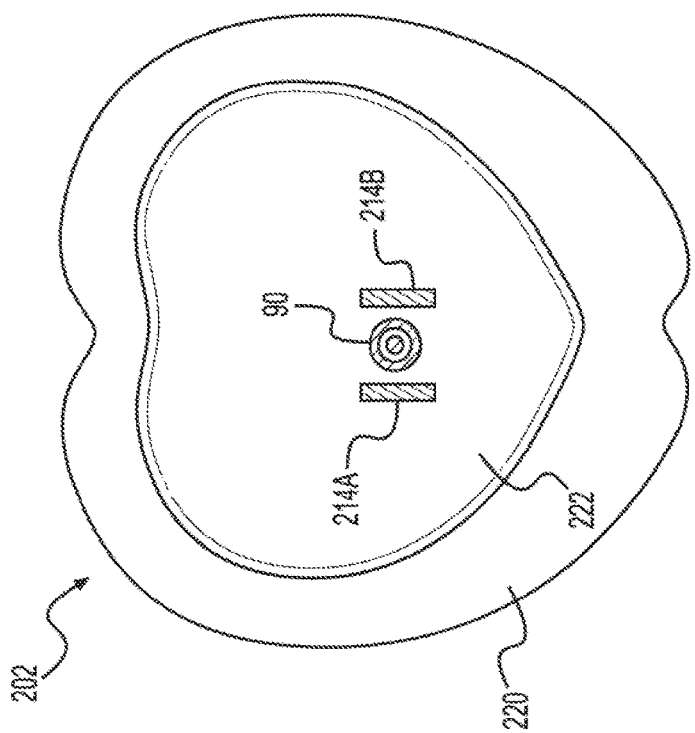
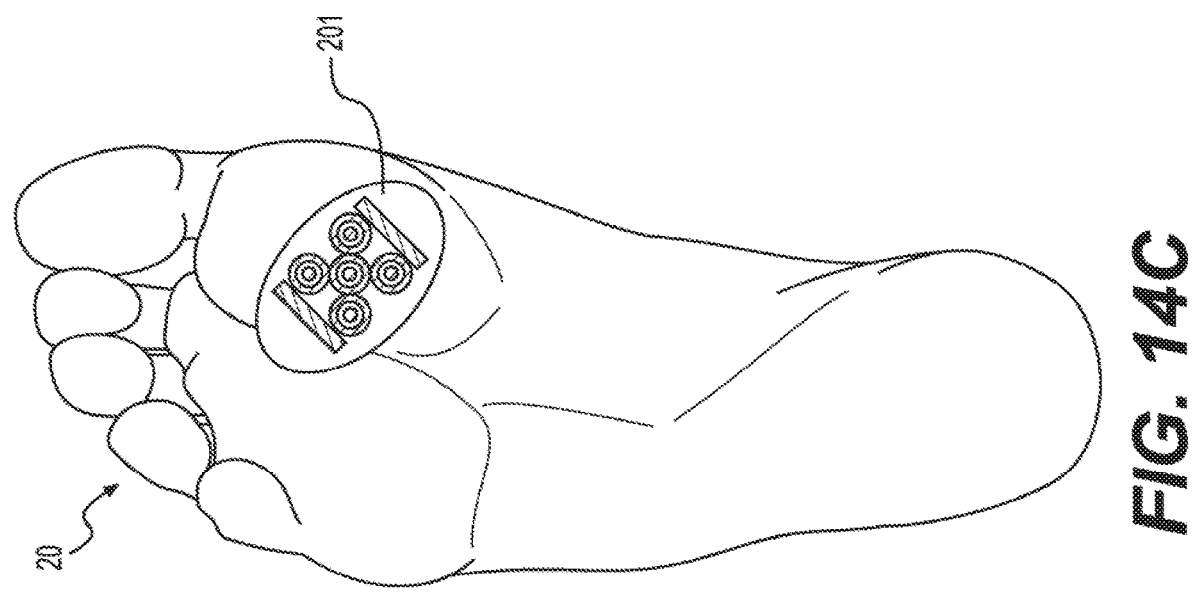
FIG. 14D
FIG. 14C

MEASUREMENT OF SUSCEPTIBILITY TO DIABETIC FOOT ULCERS

CROSS-REFERENCE TO RELATED APPLICATIONS

This application is a continuation application of U.S. application Ser. No. 15/887,886, filed on Feb. 2, 2018, which claims the benefit of priority of U.S. Provisional Application 62/454,482 filed Feb. 3, 2017, and U.S. Provisional Application 62/521,917 filed Jun. 19, 2017, each of which is herein incorporated by reference in its entirety.

FIELD

The present disclosure provides apparatus and methods for assessment of a foot of a patient at risk for development of diabetic foot ulcers.

DESCRIPTION OF THE RELATED ART

Diabetic foot ulcers are responsible for more hospitalizations than any other complication of diabetes. Nonenzymatic glycation induced by an elevated level of blood sugar causes ligaments to stiffen and increases cross-linking in collagen. These conditions can lead to damage to cellular walls and blood vessels that result in an initial increase the amount of extracellular fluid (ECF). Peripheral neuropathy causes loss of protective sensation and loss of coordination of muscle groups in the foot and leg. The neuropathy can cause an increase in the mechanical stresses within the foot during ambulation and standing that, combined with the weakened tissue induced by the diabetes, will progress to tissue death if the stress is not reduced. The neuropathy also reduces the patient's ability to perceive pain that is normally associated with the stress and tissue damage, thereby allowing the condition to progress.

Every year, approximately 5% of diabetics develop a foot ulcer and 1% will require amputation of a digit or some portion of the foot. Long term, 15% of patients with diabetes will develop a foot ulcer and 12-24% will require amputation. Diabetes is the leading cause of nontraumatic lower extremity amputations in the United States. 20-30% of the overall cost of treating diabetes is related to the treatment and healing of foot ulcers after they occur.

The current approach to the prevention of diabetic foot ulcers is patient education, foot skin and toenail care, appropriate footwear selection, and proactive surgical intervention. A means of detecting a pre-ulcer condition would enable implementation of preventive techniques such as offloading and improved hygiene.

SUMMARY

In an aspect, the present disclosure provides for, and includes, an apparatus for assessing susceptibility of tissue to formation of a diabetic foot ulcer, the apparatus comprising: a plurality of electrodes embedded on a substrate, where a pair of the electrodes is capable of forming a capacitive sensor configured to measure a first capacitance of a first region of tissue proximate to the capacitive sensor, a circuit electronically coupled to the electrodes, a processor electronically coupled to the circuit, and a non-transitory computer-readable medium electronically coupled to the processor and comprising instructions stored thereon that, when executed on the processor, perform the steps of: receiving information from the circuit regarding the measured first capacitance from the capacitive sensor, comparing the measured first capacitance to a first reference value, and providing a signal if the measured first capacitance differs from the first reference value by an amount greater than a first predetermined threshold.

In one aspect, the present disclosure provides for, and includes, a method for assessing susceptibility of tissue to formation of a diabetic foot ulcer, the method comprising: obtaining a first capacitance value at a first location of a patient's skin; obtaining a temperature measurement at the first location of a patient's skin; and determining that the first location of a patient's skin is susceptible to formation of a diabetic foot ulcer when the first capacitance value differs from the first reference value by an amount greater than a first predetermined threshold and the temperature measurement differs from the second reference value by an amount greater than a second predetermined threshold.

In an aspect, the present disclosure provides for, and includes, a method for assessing susceptibility of tissue to formation of a diabetic foot ulcer, the method comprising: obtaining a first sub-epidermal moisture (SEM) value at a first location of a patient's skin; obtaining a temperature measurement at the first location of a patient's skin; and determining that the first location of a patient's skin is susceptible to formation of a diabetic foot ulcer when the first SEM value differs from the first reference value by an amount greater than a first predetermined threshold and the temperature measurement differs from the second reference value by an amount greater than a second predetermined threshold.

In one aspect, the present disclosure provides for, and includes, an integrated apparatus for treating a diabetic foot ulcer in a patient in need thereof, said apparatus comprising: a plurality of sensors disposed on a flexible substrate, wherein the plurality of sensors are configured to measure sub-epidermal moisture (SEM) values at respective locations of the patient's skin; two electrodes disposed on the flexible substrate; and an external controller electrically connected to the two electrodes, where the external controller controls the two electrodes to detect conductive contact with the patient's skin during a SEM measurement period, and the external controller controls the two electrodes to apply a therapeutic stimulus to the patient during a therapeutic phase.

In an aspect, the present disclosure provides for, and includes, an integrated apparatus for treating a diabetic foot ulcer in a patient in need thereof, the apparatus comprising: a sensor comprising two electrodes disposed on a flexible substrate such that a current passing between the electrodes will pass through tissue proximate to a location of the patient's skin; and an external controller electrically connected to the two electrodes.

BRIEF DESCRIPTION OF THE DRAWINGS

Aspects of the disclosure are herein described, by way of example only, with reference to the accompanying drawings. With specific reference now to the drawings in detail, it is stressed that the particulars shown are by way of example and are for purposes of illustrative discussion of aspects of the disclosure. In this regard, the description and the drawings, considered alone and together, make apparent to those skilled in the art how aspects of the disclosure may be practiced.

FIG. 7A depicts a first example of a mat assembly that incorporates a plurality of bioimpedance sensors according to the present disclosure.

FIG. 7B depicts a second example of a mat assembly that comprises arrays of electrical sensors, according to the present disclosure, disposed so as to underlie the left and right feet, respectively, of a patient while standing on the mat assembly.

FIG. 7C depicts a third example of a mat assembly that comprises one or more sensors disposed within each of the outlines according to the present disclosure.

FIG. 11A shows an exemplary configuration of a substrate shaped to be positioned in a known position on a patient's skin according to the present disclosure.

FIG. 11B shows a front view of the exemplary configuration of FIG. 11A according to the present disclosure.

FIGS. 14A, 14B, and 14C depict an integrated sensor and stimulator assembly suitable for treatment of a pressure ulcer, according to the present disclosure.

FIG. 14D depicts a bandage assembly suitable for treatment of a pressure ulcer, according to the present disclosure.

DETAILED DESCRIPTION

Figure 1A:
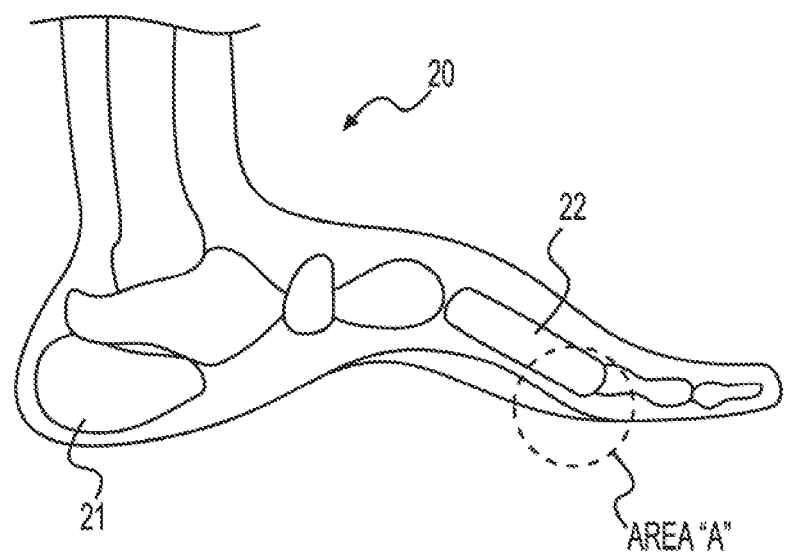
FIG. 1A depicts the anatomy of a foot.

The present disclosure describes measurement of various electrical characteristics and derivation of SEM values indicative of an increase in the amount of ECF and the application of this information to the assessment of susceptibility to diabetic foot ulcers as well as treatment of ulcers.

Diabetic foot ulcers are known to occur in areas subject to repetitive moderate loads, particularly in areas where bony portions of the foot apply transfer body weight to the adjacent tissue while standing. Damage may initially occur in tissue below the skin and is, therefore, not detectable by visual inspection. The initial damage will release fluid into the extracellular spaces, which can be detected through the measurement of electrical properties of the sub-epidermal tissue, for example the capacitance of the tissue. Monitoring the ECF in at-risk areas will detect deterioration of the tissue that, if left unchecked, will progress to an open ulcer.

This description is not intended to be a detailed catalog of all the different ways in which the disclosure may be implemented, or all the features that may be added to the instant disclosure. For example, features illustrated with respect to one embodiment may be incorporated into other embodiments, and features illustrated with respect to a particular embodiment may be deleted from that embodiment. Thus, the disclosure contemplates that in some embodiments of the disclosure, any feature or combination of features set forth herein can be excluded or omitted. In addition, numerous variations and additions to the various embodiments suggested herein will be apparent to those skilled in the art in light of the instant disclosure, which do not depart from the instant disclosure. In other instances, well-known structures, interfaces, and processes have not been shown in detail in order not to unnecessarily obscure the invention. It is intended that no part of this specification be construed to effect a disavowal of any part of the full scope of the invention. Hence, the following descriptions are intended to illustrate some particular embodiments of the disclosure, and not to exhaustively specify all permutations, combinations and variations thereof.

Unless otherwise defined, all technical and scientific terms used herein have the same meaning as commonly understood by one of ordinary skill in the art to which this disclosure belongs. The terminology used in the description of the disclosure herein is for the purpose of describing particular aspects or embodiments only and is not intended to be limiting of the disclosure.

All publications, patent applications, patents and other references cited herein are incorporated by reference in their entireties for the teachings relevant to the sentence and/or paragraph in which the reference is presented. References to techniques employed herein are intended to refer to the techniques as commonly understood in the art, including variations on those techniques or substitutions of equivalent techniques that would be apparent to one of skill in the art.

U.S. patent application Ser. No. 14/827,375 discloses an apparatus that uses radio frequency (RF) energy to measure the sub-epidermal capacitance using a bipolar sensor similar to the sensor 90 shown in FIG. 3A, where the sub-epidermal capacitance corresponds to the moisture content of the target region of skin of a patient. The '375 application also discloses an array of these bipolar sensors of various sizes.

U.S. patent application Ser. No. 15/134,110 discloses an apparatus for measuring sub-epidermal moisture (SEM) similar to the device shown in FIG. 3C, where the device emits and receives an RF signal at a frequency of 32 kHz through a single coaxial sensor and generates a bioimpedance signal, then converts this signal to a SEM value.

Both U.S. patent application Ser. Nos. 14/827,375 and 15/134,110 are incorporated herein by reference in their entireties.

Unless the context indicates otherwise, it is specifically intended that the various features of the disclosure described herein can be used in any combination. Moreover, the present disclosure also contemplates that in some embodiments of the disclosure, any feature or combination of features set forth herein can be excluded or omitted.

The methods disclosed herein include and comprise one or more steps or actions for achieving the described method. The method steps and/or actions may be interchanged with one another without departing from the scope of the present invention. In other words, unless a specific order of steps or actions is required for proper operation of the embodiment, the order and/or use of specific steps and/or actions may be modified without departing from the scope of the present invention.

As used in the description of the disclosure and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The terms "about" and "approximately" as used herein when referring to a measurable value such as a length, a frequency, or a SEM value and the like, is meant to encompass variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

As used herein, the term "sub-epidermal moisture" or "SEM" refers to the increase in tissue fluid and local edema caused by vascular leakiness and other changes that modify the underlying structure of the damaged tissue in the presence of continued pressure on tissue, apoptosis, necrosis, and the inflammatory process.

As used herein, a "system" may be a collection of devices in wired or wireless communication with each other.

As used herein, "interrogate" refers to the use of radiofrequency energy to penetrate into a patient's skin.

As used herein, a "patient" may be a human or animal subject.

As used herein, "healthy" may describes tissue that does not exhibit symptoms of damage to cellular walls or blood vessels, where the presence of an increased amount of ECF is an indication of such damage.

As used herein, "extracellular fluid" or "ECF" refers to bodily fluid contained outside of cells, including plasma, interstitial fluid, and transcellular fluid.

As used herein, "susceptible to formation of a diabetic foot ulcer" may describe tissue that exhibit symptoms of damage to cellular walls or blood vessels, such as edema or an increased amount of ECF, yet no open ulcer is present.

As used herein, "time_0" refers to an initial time point, for example, when an open ulcer is first detected.

As used herein, "time_1" refers to a time point later than time_0.

As used herein, "time_2" refers to a time point later than time_1.

FIG. 1A is a side view of a portion of the anatomy of a foot 20. The areas of the foot that are most likely to develop a diabetic foot ulcer are the heel, located below the calcaneus bone 21, and the pad of the foot, located under the metatarsal bone 22.

Figure 1B:
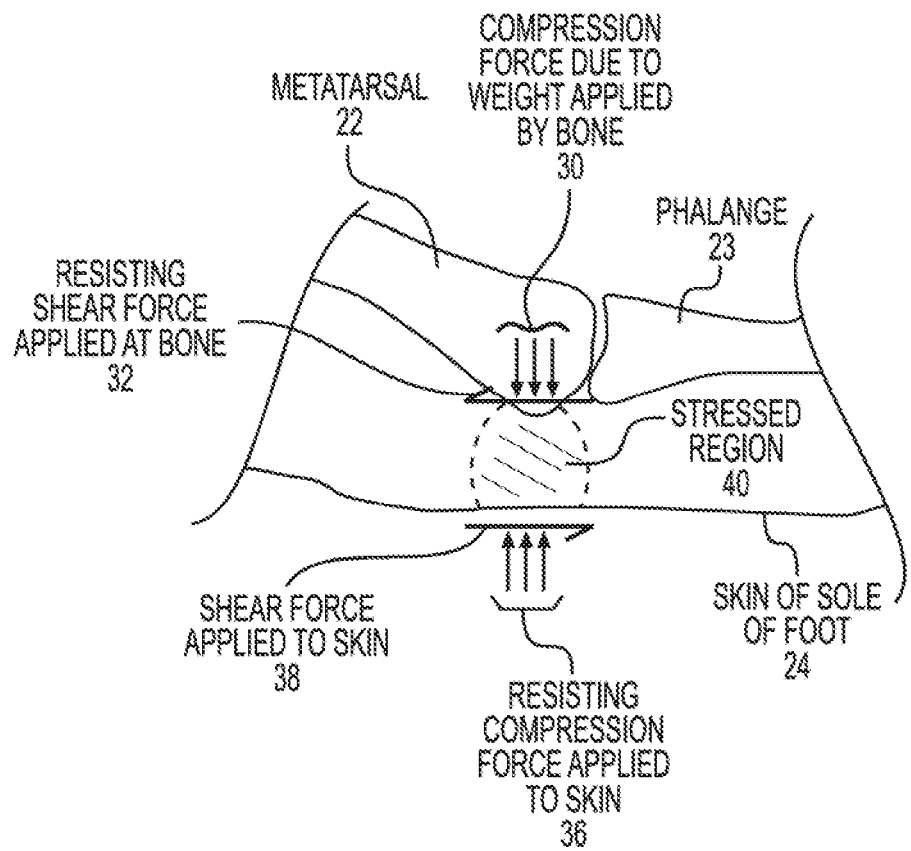
FIG. 1B is an enlarged view of area A of FIG. 1A.

FIG. 1B is an enlarged view of the area "A" of FIG. 1A. The ends of the metatarsal bone 22 and the adjoining phalange bone 23 are shown in proximity to the skin 24 of the sole of the foot 20. A portion of the body weight of the patient creates a compressive force 30 applied by the metatarsal bone 22 to the tissue in region 40. Force 30 is opposed by resistive force 36 applied by the floor to the skin 24 under region 40 to support the patient. Muscular activity by the patient, for example walking or simply balancing on their feet while standing, creates shear force 32 between the metatarsal bone 22 and tissue 40 as well as the resisting shear force 38 between the floor and the skin 24. Thus, the tissue in region 40 is simultaneously subject to both compression and shear forces.

It has been observed that a healthy patient will shift their weight from foot to foot as well as shift their center of mass relative to their feet while standing stationary. This limits the duration of time during which forces are applied to any particular region of tissue. Peripheral neuropathy, however, reduces the sensation in the tissue that is created by the patient's weight and, therefore, reduces the unconscious shifting of their weight and patients suffering from peripheral neuropathy are observed to lack the normal motion while standing. This leads to extended period of time of continuous compressive force being applied to local areas of tissue, such as region 40. This extended exposure to moderate levels of force is thought to contribute to the formation of ulcers in these areas.

Figure 2A:
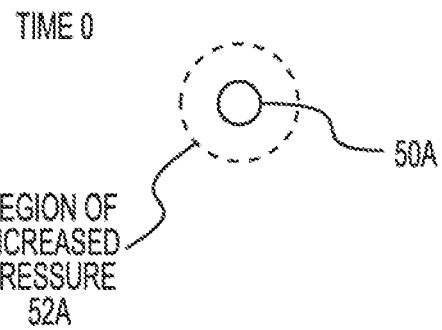
FIG. 2A depicts an initial open ulcer at time_0.

FIGS. 2A, 2B, 2C, and 2D depict the conditions and progression of an open ulcer. FIG. 2A depicts an initial open ulcer 50A at time_0. The ulcer 50A is surrounded by a ring of increased pressure 52A.

Figure 2B:
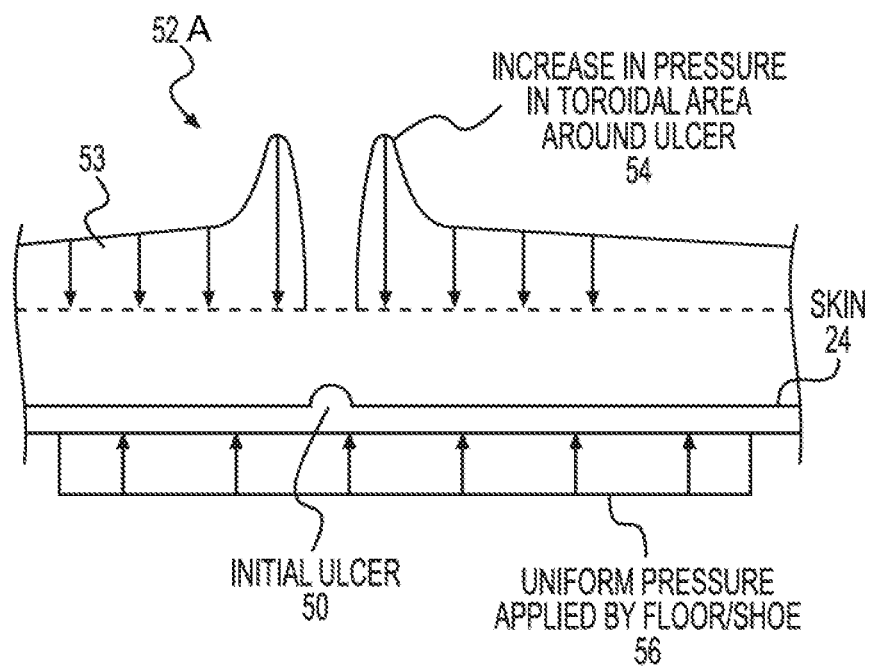
FIG. 2B depicts the pressure profile created in the condition of FIG. 2A.

FIG. 2B shows the pressure profile created in the condition of FIG. 2A. The force applied by the floor, or by a shoe worn by the patient, is applied as a locally uniform pressure 56 to the skin 24 of the foot 20. The applied pressure 56 is opposed internally by forces 53. No pressure can be applied over the ulcer 50, as the tissue has sloughed away. Thus, the internal forces in the toroidal region 52A increase to a peak 54 to pick up the force that would have been applied to the ulcer 50. This peak force 54 is high enough to cause further tissue damage in the ring 52A. A callus will commonly form over the region 52A as the body attempts to protect itself from the increased pressure. The tissue below the callus, however, is still being damaged and will exhibit an increase in ECF.

Figure 2C:
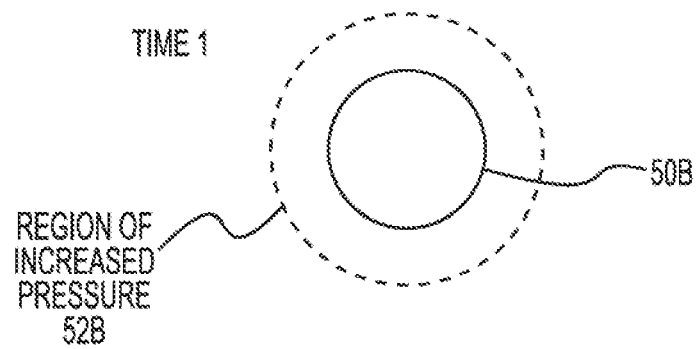
FIG. 2C depicts the same region of tissue of FIG. 2A at time_1.

FIG. 2C depicts the same region of tissue at time_1 that is subsequent to time_0. The increased level of pressure in region 52A led to tissue death in region 52A and the tissue in region 52 has sloughed away so that the ulcer 50B is larger than the prior ulcer 50A. The applied pressure 56 has not changed, however, so now the tissue in the region 52B around the larger ulcer 50B must pick up even more force. This accelerates the expansion of the ulcer 50 as the tissue in are region 52B dies quicker under the higher applied load.

Figure 2D:
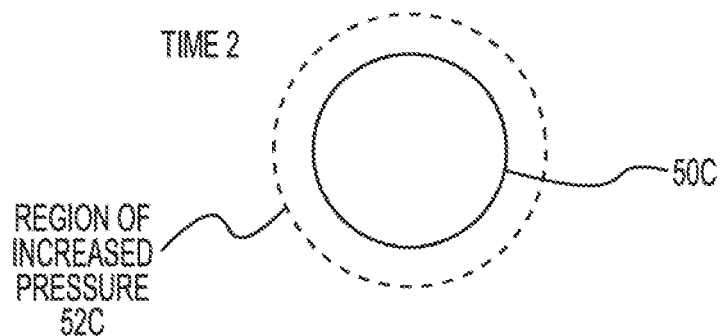
FIG. 2D depicts the same region of tissue of FIGS. 2A and 2C at time_2.

FIG. 2D depicts the same region of tissue as FIGS. 2A and 2C, now at time_2 that is subsequent to time_1. The ulcer 50 has grown to size 50C and the region 52C of increased pressure is large than the prior regions 52A, 52B.

In the situation shown in FIG. 2A, where an ulcer has formed, interventional therapies will be introduced to prevent the growth of the ulcer 50 and allow the body to heal the open ulcer 50. Therapies may involve placing pressure-relieving pads around the ulcer to spread the pressure 56 over a larger region of healthy tissue and eliminate the peak 54 that leads to further damage. Determining whether the therapy is working, however, is only possible by observation over time that the ulcer is not progressing.

Figure 3A:
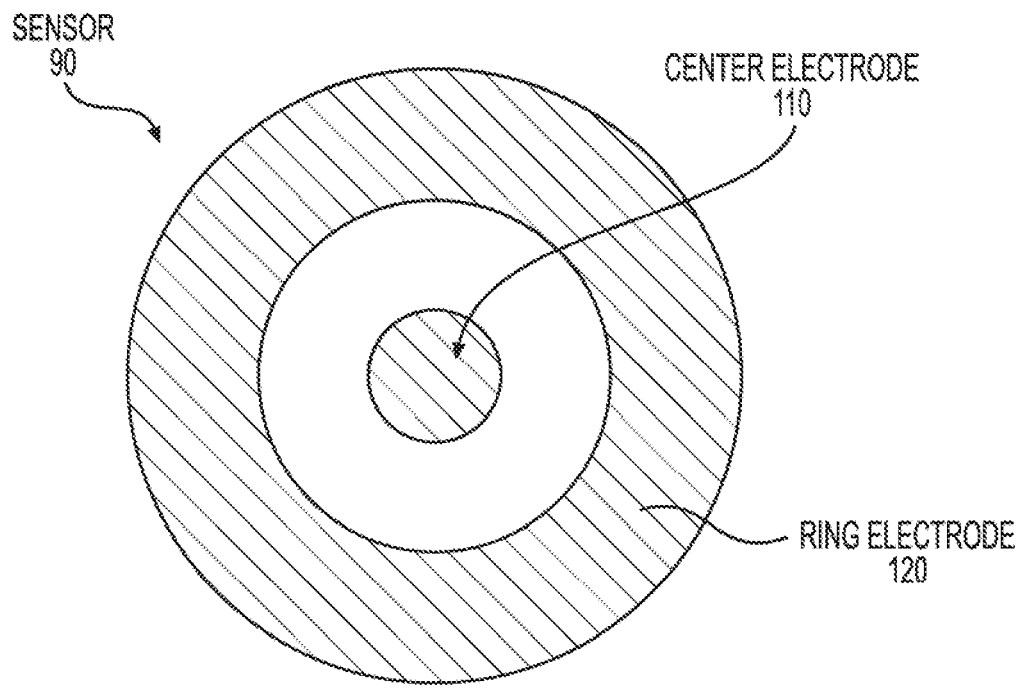
FIG. 3A discloses a toroidal bioimpedance sensor.

FIG. 3A discloses a toroidal bioimpedance sensor 90. In this exemplary configuration, a center electrode 110 is surrounded by a ring electrode 120. Without being limited to a particular theory, the gap between the two electrodes affects the depth of field penetration into the substrate below sensor 90. In one aspect, a ground plane (not visible in FIG. 3A), is parallel to and separate from the plane of the electrodes and, in an aspect, extends beyond the outer diameter of ring electrode 120. Without being limited to a particular theory, a ground plane may limit the field between electrodes 110 and 120 to a single side of the plane of electrodes 110 and 120 that is on the opposite side of the plane of electrodes 110 and 120 from the ground plane.

Figure 3B:
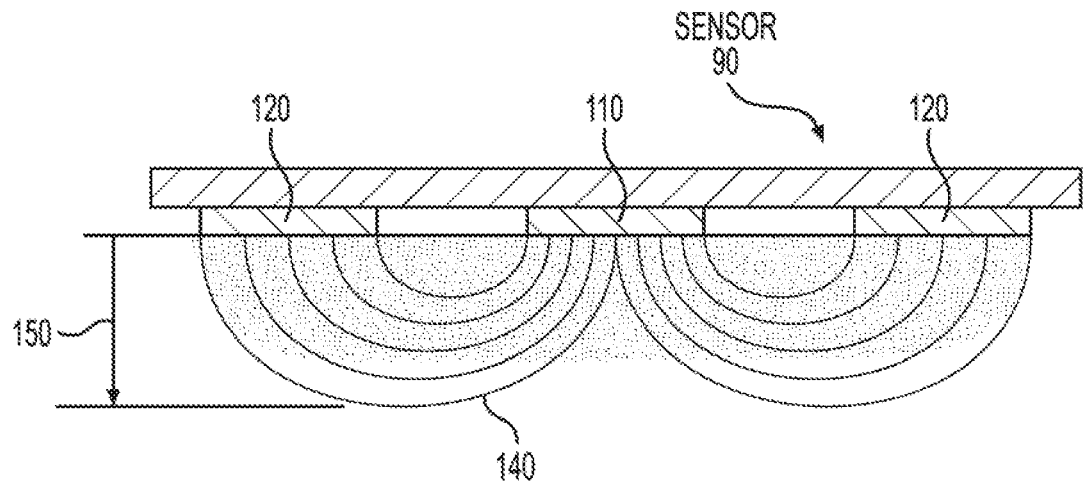
FIG. 3B discloses an idealized field map created by the toroidal sensor of FIG. 3A when activated.

FIG. 3B discloses an idealized field map created by a toroidal sensor of FIG. 3A when activated by a drive circuit (not shown in FIG. 3B). When an electric voltage is applied across electrodes 110 and 120, an electric field 140 is generated between electrodes 110 and 120 that extends outward from the plane of electrodes 110 and 120 to a depth of field 150. The diameter of center electrode 110, the inner and outer diameters of ring electrode 120, and the gap between electrodes 110 and 120 may be varied to change characteristics of the field 140, for example the depth of field 150.

In use, a drive circuit can measure an electrical property or parameter that comprises one or more electrical characteristics selected from the group consisting of a resistance, a capacitance, an inductance, an impedance, a reluctance, and other electrical characteristics as sensed by electric field 140. Depending on the type of drive circuit being employed in an apparatus, a sensor of an apparatus may be a bipolar radiofrequency sensor, a bioimpedance sensor, a capacitive sensor, or an SEM sensor. In an aspect, a measured electrical parameter is related to the moisture content of the epidermis of a patient at a depth that is determined by the geometry of electrodes 110 and 120, the frequency and strength of electrical field 140, and other operating characteristics of the apparatus drive circuit. In one aspect, a measured moisture content is equivalent to the SEM content with a value on a predetermined scale. In an aspect, a predetermined scale may range from 0 to 20, such as from 0 to 1, from 0 to 2, from 0 to 3, from 0 to 4, from 0 to 5, from 0 to 6, from 0 to 7, from 0 to 8, from 0 to 9, from 0 to 10, from 0 to 11, from 0 to 12, from 0 to 13, from 0 to 14, from 0 to 15, from 0 to 16, from 0 to 17, from 0 to 18, from 0 to 19. In one aspect, a predetermined scaled can be scaled by a factor or a multiple based on the values provided herein. In an aspect, multiple measurements are taken while varying one or more of these operating characteristics between readings, thereby providing information related to the moisture content at various depths of the skin.

One or more regions may be defined on a body. In an aspect, measurements made within a region are considered comparable to each other. A region may be defined as an area on the skin of the body wherein measurements may be taken at any point within the area. In an aspect, a region corresponds to an anatomical region (e.g., heel, ankle, lower back). In an aspect, a region may be defined as a set of two or more specific points relative to anatomical features wherein measurements are taken only at the specific points. In an aspect, a region may comprise a plurality of non-contiguous areas on the body. In an aspect, the set of specific locations may include points in multiple non-contiguous areas.

In an aspect, a region is defined by surface area. In an aspect, a region may be, for example, between 5 and 200 $cm^2$, between 5 and 100 $cm^2$, between 5 and 50 $cm^2$, or between 10 and 50 $cm^2$, between 10 and 25 $cm^2$, or between 5 and 25 $cm^2$.

In an aspect, measurements may be made in a specific pattern or portion thereof. In an aspect, the pattern of readings is made in a pattern with the target area of concern in the center. In an aspect, measurements are made in one or more circular patterns of increasing or decreasing size, T-shaped patterns, a set of specific locations, or randomly across a tissue or region. In an aspect, a pattern may be located on the body by defining a first measurement location of the pattern with respect to an anatomical feature with the remaining measurement locations of the pattern defined as offsets from the first measurement position.

In an aspect, a plurality of measurements are taken across a tissue or region and the difference between the lowest measurement value and the highest measurement value of the plurality of measurements is recorded as a delta value of that plurality of measurements. In an aspect, 3 or more, 4 or more, 5 or more, 6 or more, 7 or more, 8 or more, 9 or more, or 10 or more measurements are taken across a tissue or region.

In an aspect, a threshold may be established for at least one region. In an aspect, a threshold of 0.2, 0.3, 0.4, 0.5, 0.6, 0.7, 0.8, 0.9, or other value may be established for the at least one region. In an aspect, a delta value is identified as significant when the delta value of a plurality of measurements taken within a region meets or exceeds a threshold associated with that region. In an aspect, each of a plurality of regions has a different threshold. In an aspect, two or more regions may have a common threshold.

In an aspect, a threshold has both a delta value component and a chronological component, wherein a delta value is identified as significant when the delta value is greater than a predetermined numerical value for a predetermined portion of a time interval. In an aspect, the predetermined portion of a time interval is defined as a minimum of X days wherein a plurality of measurements taken that day produces a delta value greater than or equal to the predetermined numerical value within a total of Y contiguous days of measurement. In an aspect, the predetermined portion of a time interval may be defined as 1, 2, 3, 4, or 5 consecutive days on which a plurality of measurements taken that day produces a delta value that is greater than or equal to the predetermined numerical value. In an aspect, the predetermined portion of a time interval may be defined as some portion of a different specific time period (weeks, month, hours etc.).

In an aspect, a threshold has a trending aspect wherein changes in the delta values of consecutive pluralities of measurements are compared to each other. In an aspect, a trending threshold is defined as a predetermined change in delta value over a predetermined length of time, wherein a determination that the threshold has been met or exceeded is significant. In an aspect, a determination of significance will cause an alert to be issued. In an aspect, a trend line may be computed from a portion of the individual measurements of the consecutive pluralities of measurements. In an aspect, a trend line may be computed from a portion of the delta values of the consecutive pluralities of measurements.

In an aspect, the number of measurements taken within a single region may be less than the number of measurement locations defined in a pattern. In an aspect, a delta value will be calculated after a predetermined initial number of readings, which is less than the number of measurement locations defined in a pattern, have been taken in a region and after each additional reading in the same region, wherein additional readings are not taken once the delta value meets or exceeds the threshold associated with that region.

In an aspect, the number of measurements taken within a single region may exceed the number of measurement locations defined in a pattern. In an aspect, a delta value will be calculated after each additional reading.

In an aspect, a quality metric may be generated for each plurality of measurements. In an aspect, this quality metric is chosen to assess the repeatability of the measurements. In an aspect, this quality metric is chosen to assess the skill of the clinician that took the measurements. In an aspect, the quality metric may include one or more statistical parameters, for example an average, a mean, or a standard deviation. In an aspect, the quality metric may include one or more of a comparison of individual measurements to a predefined range. In an aspect, the quality metric may include comparison of the individual measurements to a pattern of values, for example comparison of the measurement values at predefined locations to ranges associated with each predefined location. In an aspect, the quality metric may include determination of which measurements are made over healthy tissue and one or more evaluations of consistency within this subset of "healthy" measurements, for example a range, a standard deviation, or other parameter.

In one aspect, a measurement, for example, a threshold value, is determined by SEM Scanner Model 200 (Bruin Biometrics, LLC, Los Angeles, Calif.). In another aspect, a measurement is determined by another SEM scanner.

In an aspect, a measurement value is based on a capacitance measurement by reference to a reference device. In an aspect, a capacitance measurement can depend on the location and other aspects of any electrode in a device. Such variations can be compared to a reference SEM device such as an SEM Scanner Model 200 (Bruin Biometrics, LLC, Los Angeles, Calif.). A person of ordinary skill in the art understands that the measurements set forth herein can be adjusted to accommodate a difference capacitance range by reference to a reference device.

Figure 3C:
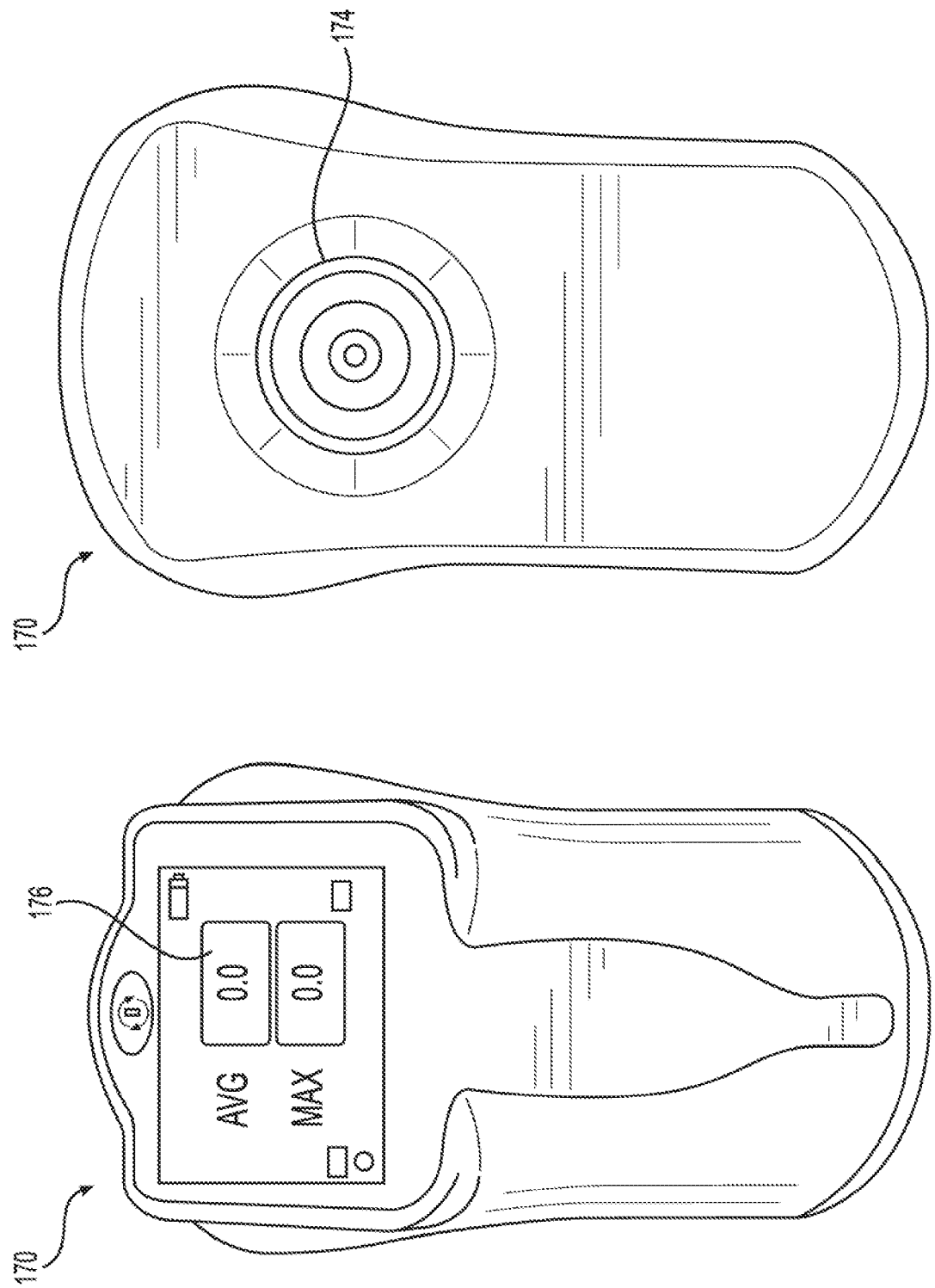
FIG. 3C discloses a SEM scanner that comprises the sensor of FIG. 3A.

FIG. 3C provides top and bottom views of a SEM scanner 170 that contains electronics that drive sensor 174, which is similar to sensor 90 of FIG. 3A, and measure a capacitance between electrodes 110 and 120. This capacitance may be converted to a SEM value that is displayed on display 176.

Aspects of sensor 90 and SEM scanner 170 are disclosed in WO 2016/172263, from which the U.S. patent application Ser. No. 15/134,110 was filed as a national phase entry, all of which are incorporated by reference herein in their entireties.

Figure 4:
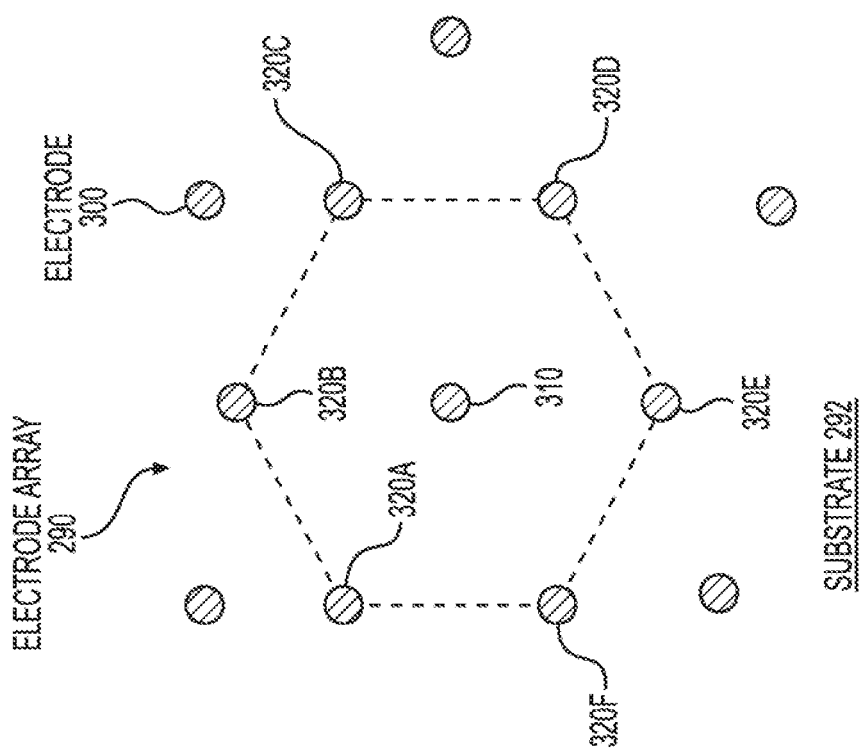
FIG. 4 is a first exemplary array of electrodes.

FIG. 4 depicts an exemplary electrode array 290, according to the present disclosure. Array 290 is composed of individual electrodes 300 disposed, in this example, in a regular pattern over a substrate 292. In an aspect, each electrode 300 is separately coupled (through conductive elements not shown in FIG. 4) to a circuit (not shown in FIG. 4) that is configured to measure an electrical parameter. In one aspect, a "virtual sensor" is created by selective connection of predetermined subsets of electrodes 300 to a common element of a circuit. In this example, a particular electrode 310 is connected as a center electrode, similar to electrode 110 of FIG. 3A, and six electrodes 320A-320F are connected together as a "virtual ring" electrode, similar to electrode 120 of FIG. 3A. In an aspect, two individual electrodes are individually connected to the circuit to form a virtual sensor, for example electrodes 310 and 320A are respectively connected as the two electrodes of a sensor. In one aspect, one or more electrodes 300 are connected together to form one or the other of the electrodes of a two-electrode sensor.

Any pair of electrodes, whether composed of single electrodes or a set of electrodes coupled together to form virtual electrodes, is coupled to electronics (not shown in FIG. 4) that are configured to measures an electrical property or parameter that comprises one or more of a resistance, a capacitance, an inductance, an impedance, a reluctance, or other electrical characteristic with one or more of sensors 90, 174, 290, 430, 440, or other two-electrode sensor. Electronics of the present disclosure may be further configured to compare the measured first capacitance to a reference value and providing a signal if the measured capacitance differs from the reference value by an amount greater than a threshold. In an aspect, one or both of the reference value and the threshold are predetermined.

Figure 5:
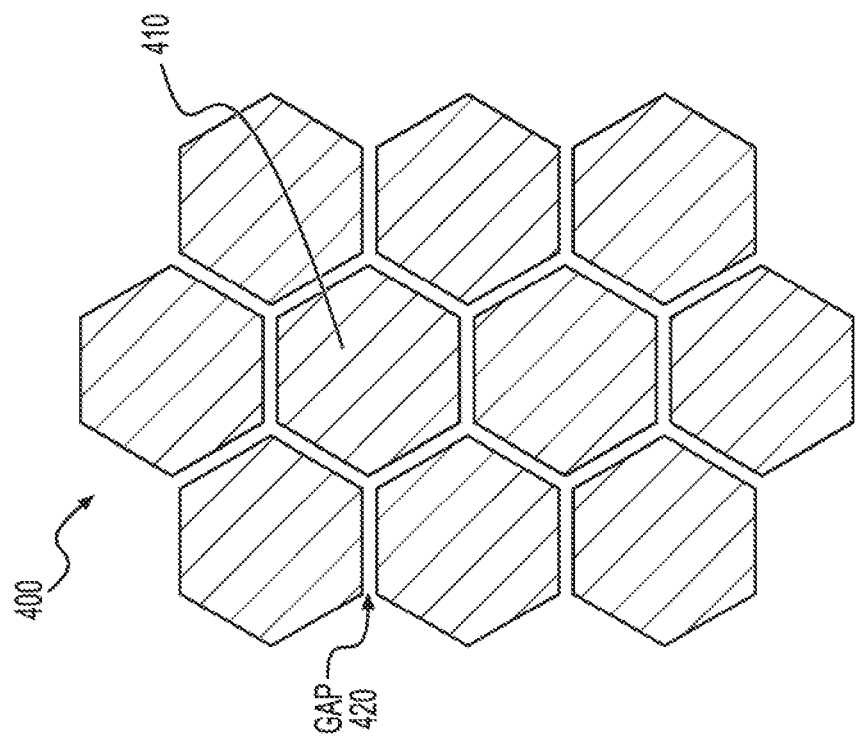
FIG. 5 is an exemplary array of electrodes according to the present disclosure.

FIG. 5 depicts another exemplary array 400 of electrodes 410, according to the present disclosure. In this non-limiting example, each of the electrodes 410 is an approximate hexagon that is separated from each of the surrounding electrodes 410 by a gap 420. In one aspect, electrodes 410 are one of circles, squares, pentagons, or other regular or irregular shapes. In an aspect, gap 420 is uniform between all electrodes 410. In one aspect, gap 420 varies between various electrodes. In one aspect, gap 420 has a width that is narrower than the cross-section of each of the electrodes 410. Electrodes 410 may be interconnected to form virtual sensors as described below with respect to FIGS. 6A-6B and 10A-10C.

Figure 6B:
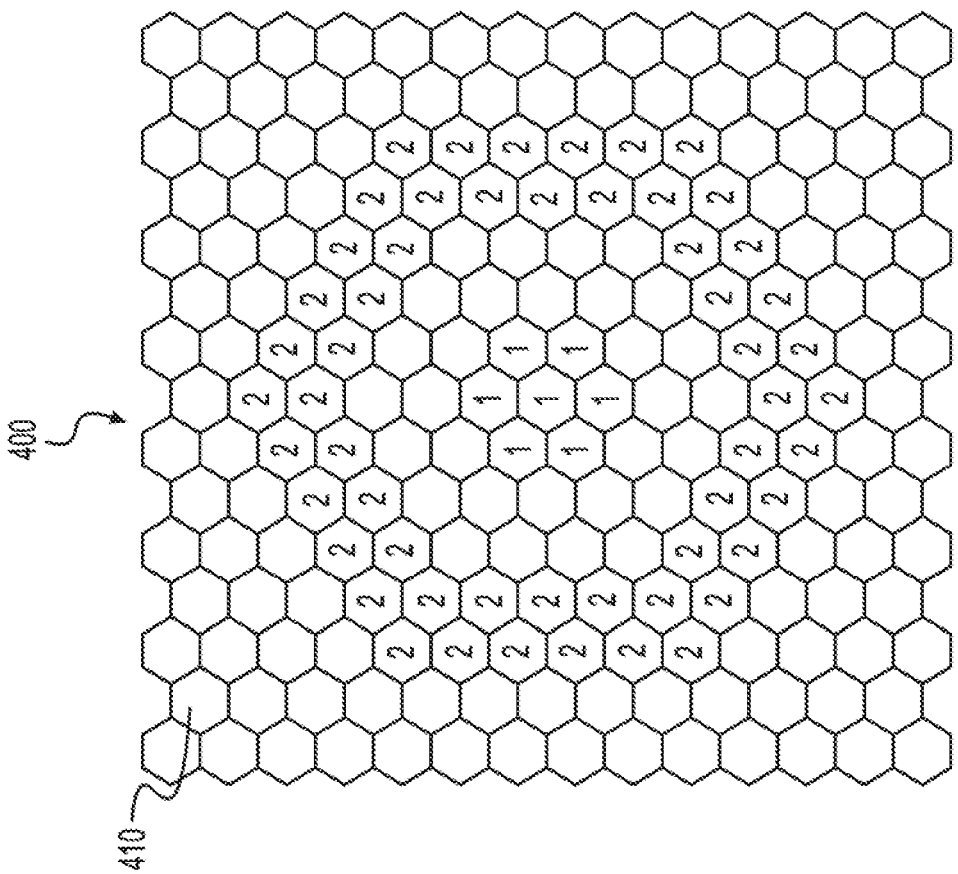
FIG. 6B illustrates a first example of how the array of electrodes disclosed in FIG. 5 is configured to form a bioimpedance sensor according to the present disclosure.
Figure 6A:
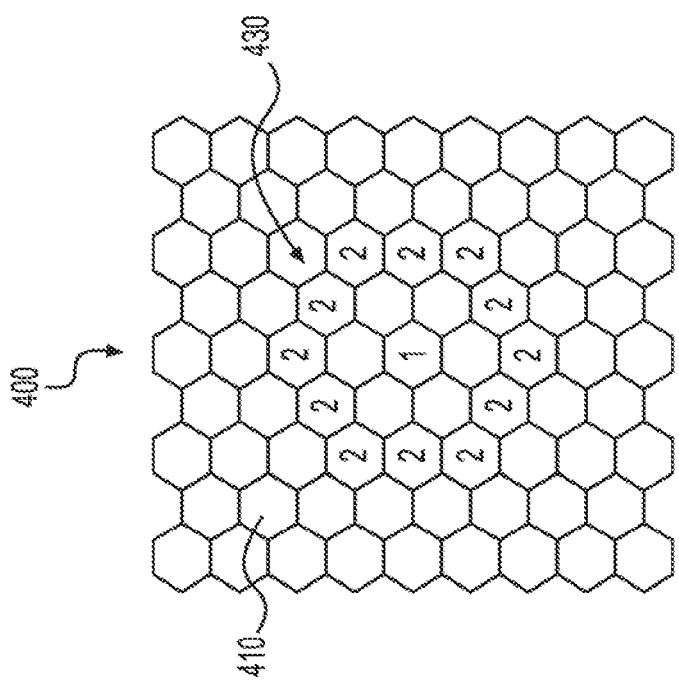
FIG. 6A illustrates a first example of how the array of electrodes disclosed in FIG. 5 is configured to form a bioimpedance sensor according to the present disclosure.
Figure 6D:
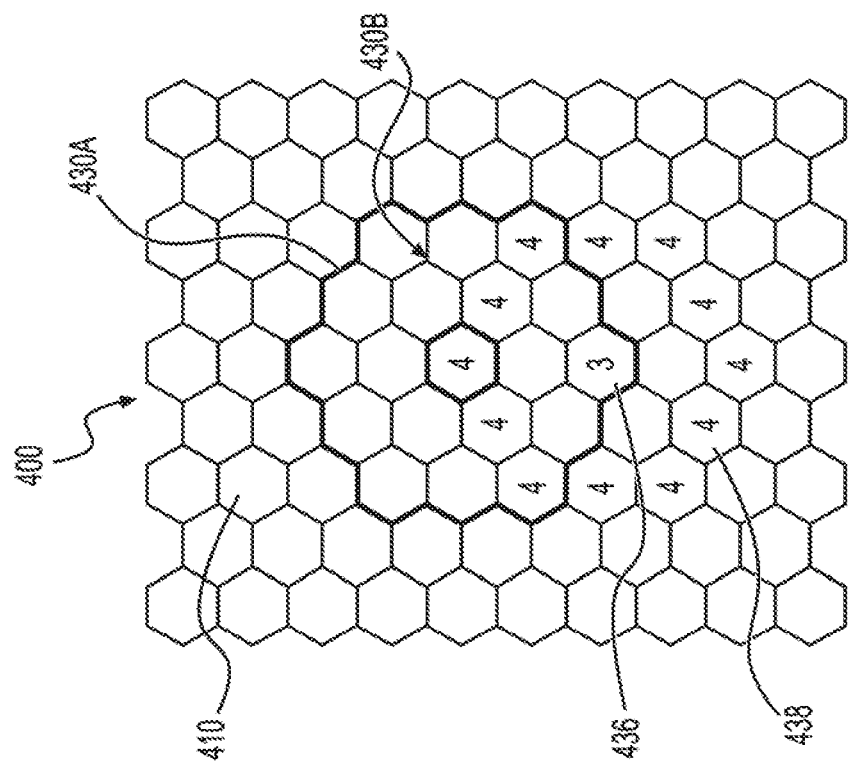
FIG. 6D illustrates an example of how a second sensor is formed to overlap with the first sensor of FIG. 6C according to the present disclosure.
Figure 6C:
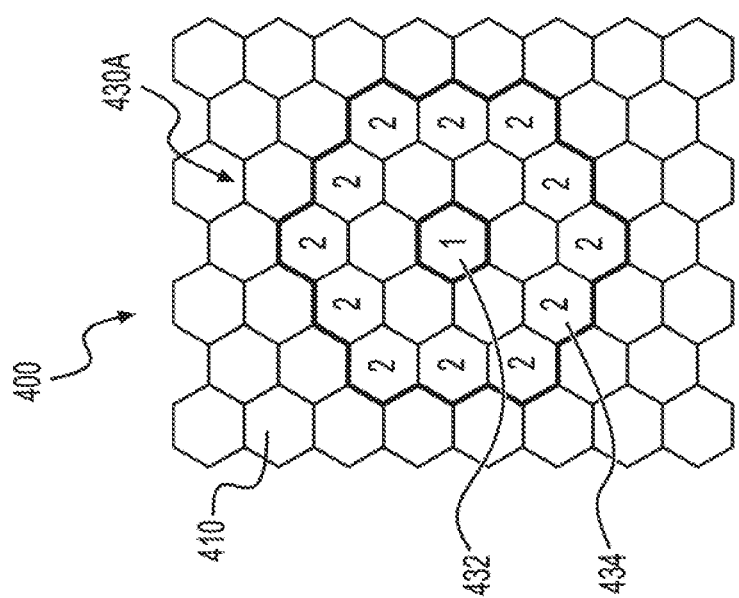
FIG. 6C illustrates an example of a first sensor formed in an array of electrodes according to the present disclosure.

FIG. 6A depicts an array 400 of electrodes 410 that are configured, e.g. connected to a measurement circuit, to form an exemplary sensor 430, according to the present disclosure. A single hexagonal electrode 410 that is labeled with a "1" forms a center electrode and a ring of electrodes 410 that are marked with a "2" are interconnected to form a ring electrode. In an aspect, electrodes 410 between the center and ring electrode are electrically "floating." In one aspect, electrodes 410 between the center and ring electrode are grounded or connected to a floating ground. In an aspect, electrodes 410 that are outside the ring electrode are electrically "floating." In one aspect, electrodes 410 that are outside a virtual ring electrode are grounded or connected to a floating ground.

FIG. 6B depicts an alternate aspect where an array 400 of electrodes 410 has been configured to form a virtual sensor 440, according to the present disclosure. In an aspect, multiple electrodes 410, indicated by a "1," are interconnected to form a center electrode while a double-wide ring of electrodes, indicated by a "2," are interconnected to form a ring electrode. In one aspect, various numbers and positions of electrodes 410 are interconnected to form virtual electrodes of a variety of sizes and shapes.

FIGS. 6A and 6B depict an exemplary configuration of an electrode array 400 that is capable of forming sensors 430 in multiple overlapping locations, according to the present disclosure. In FIG. 6A, a virtual sensor 430A has been formed with center electrode 432 formed by a single electrode 410, indicated by a "1," and a ring electrode 434 formed by a plurality of electrodes 410, indicated by a "2." This same array 400 is shown in FIG. 6B, where a new virtual sensor 430B has been formed with a center electrode 436, indicated by a "3," and ring electrode 438, indicated by a "4." The position of virtual sensor 430A is shown by the dark outline. It can be seen that virtual sensor 430B overlaps the position of virtual sensor 430A, this allowing measurements to be made at a finer resolution than the diameter of sensors 430.

Figure 6E:
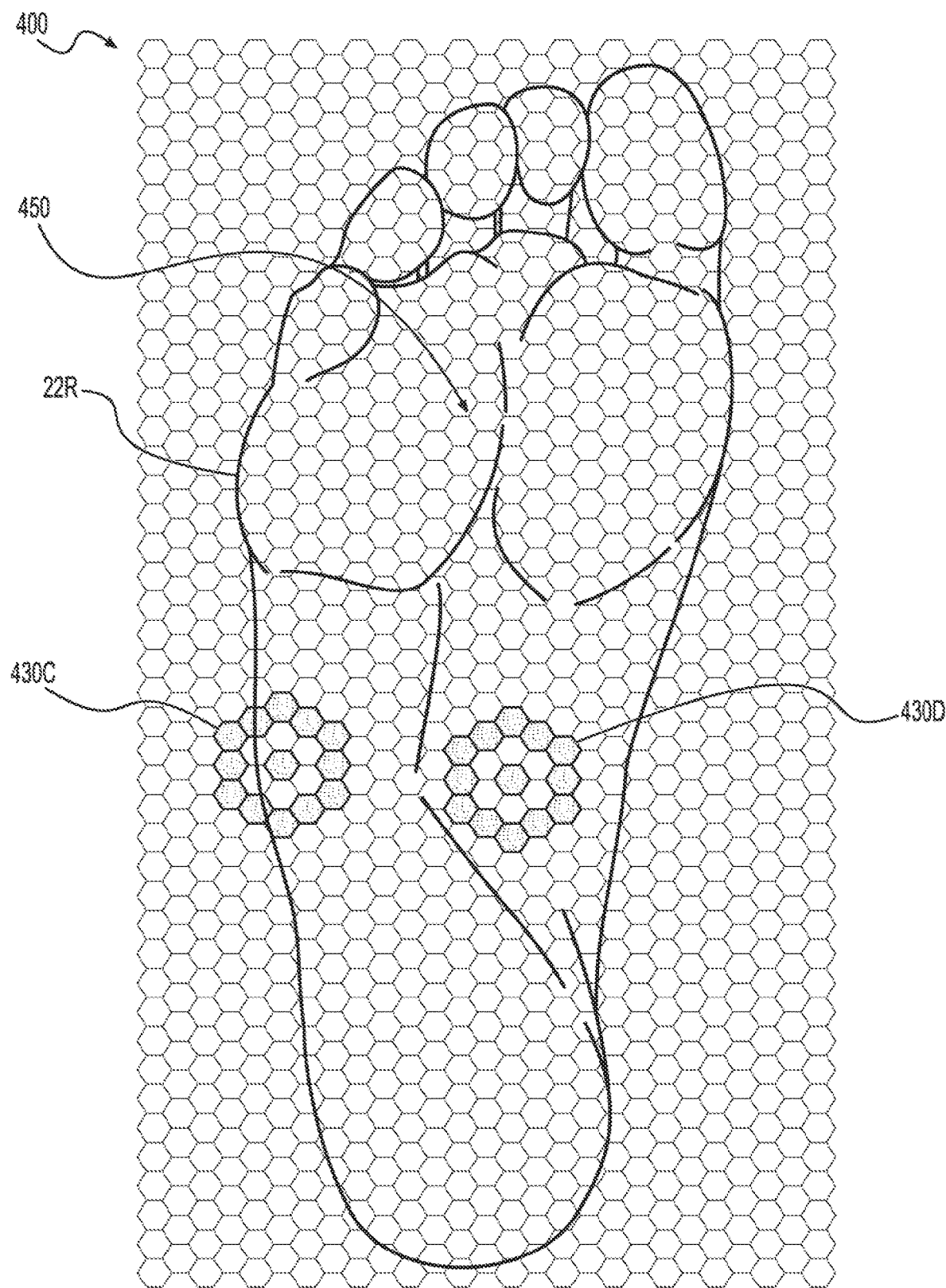
FIG. 6E shows an example of how sensors as shown in FIG. 6A are formed from an array of electrodes that is larger than the portion of the patient's skin that is being positioned against the array, according to the present disclosure.

FIG. 6E shows how sensors 430 may be formed from an array of electrodes 400 that is larger than the portion of a patient's skin that is being positioned against the array, according to the present disclosure. In this example, the outline of contact area 450 of sole 22R of a right foot of a patient, as seen from underneath the foot, is shown overlaid on array 400. In this example, sensor 430C has been formed in a location where a portion of sensor 430C extends beyond the edge of contact area 450. In such a position, the capacitance or other electrical parameter measured by sensor 430C is lower than the capacitance measured by sensor 430D, which is positioned completely within contact area 450. It can be seen that a sensor 430 may be formed at any point within array 400 and, depending on the position of sensor 430, may partially overlap the contact area at any level within the range of 0-100%.

In an aspect, two sensors may overlap 0-50%, such as 0-10%, 5-15%, 10-20%, 15-25%, 20-30%, 25-35%, 30-40%, 35%-45%, 40-50%, 0-25%, 15-35%, or 25-50%. In one aspect, two sensors may overlap 25-75%, such as 25-35%, 30-40%, 35%-45%, 40-50%, 45-55%, 50-60%, 55-65%, 60-70%, 65-75%, 25-50%, 40-55%, or 50-75%. In one aspect, two sensors may overlap 50-100%, such as 50-60%, 55-65%, 60-70%, 65-75%, 70-80%, 75%-85%, 80-90%, 85-95%, 90-100%, 50-75%, 65-85%, or 75-100%.

In one aspect, an array of sensors 400 may further comprise a plurality of contact sensors (not shown on FIG. 6E) on the same planar surface as, and surrounding, each of the electrodes to ensure complete contact of the one or more virtual sensors to the skin surface. The plurality of contact sensors may be a plurality of pressure sensors, a plurality of light sensors, a plurality of temperature sensors, a plurality of pH sensors, a plurality of perspiration sensors, a plurality of ultrasonic sensors, a plurality of bone growth stimulator sensors, or a plurality of a combination of these sensors. In some embodiments, the plurality of contact sensors may comprise four, five, six, seven, eight, nine, or ten or more contact sensors surrounding each electrode.

Figure 6F:
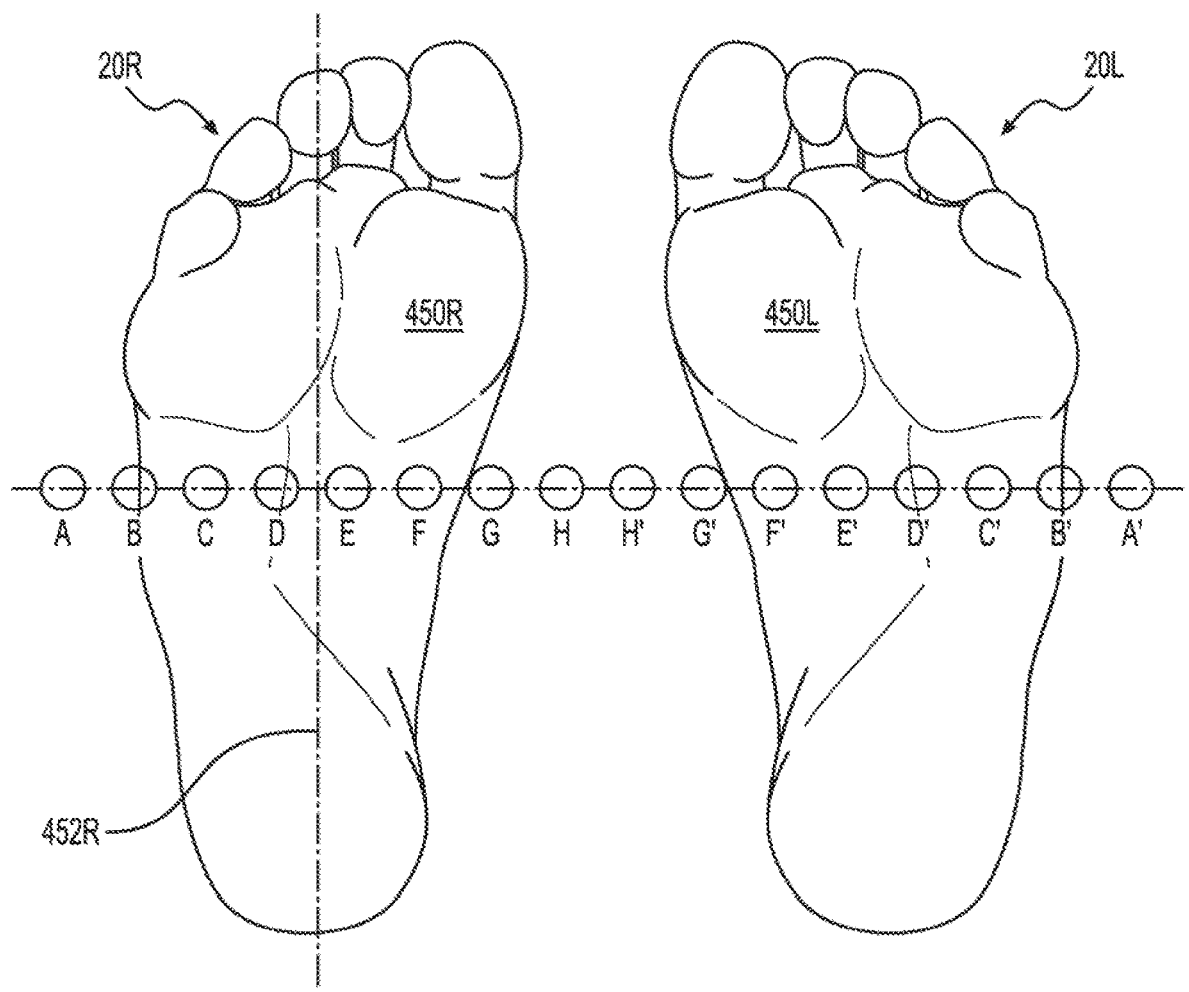
FIG. 6F illustrates locations on the left and right feet for SEM measurements according to the present disclosure.
Figure 6G:
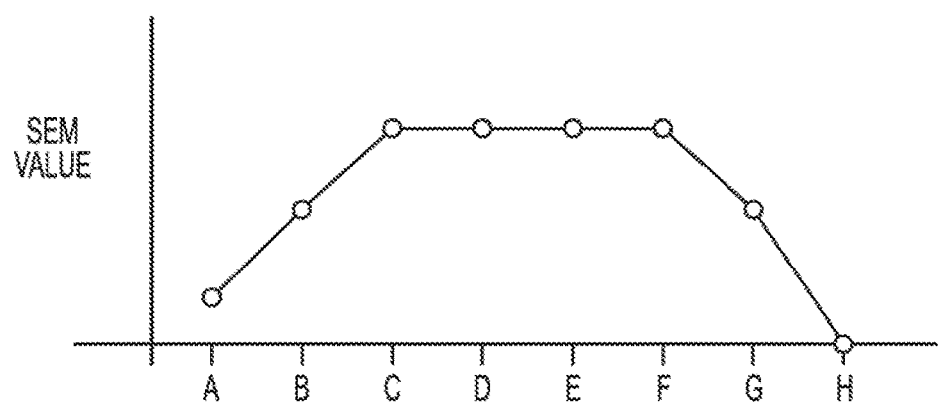
FIG. 6G is a plot of SEM values associated with known relative locations for identifying bisymmetric locations according to the present disclosure.

FIGS. 6F and 6G depict an example of how comparison of SEM values associated with sensors in known relative locations can identify bisymmetric locations, according to the present disclosure. In this example, sensors 430 are formed at non-overlapping locations, marked "A" to "H" in FIG. 6F, across a contact area 450R of a right foot 20R. The SEM values measured at each location are plotted in the graph of FIG. 6G. In this example, the SEM value of locations "A" and "H" are low or zero, reflecting the non-overlap of sensor 430 with contact area 450 in those locations. The SEM values associated with locations "B" and "G" are higher, as sensor 430 overlaps a portion of contact area 450 in those positions. The SEM values for locations C-D-E-F are higher and, in this example, approximately the same, indicating that sensor 430 was completely within contact area 450 at those locations. In an aspect, an SEM measurement apparatus such as apparatus 180 may determine that certain locations, for example locations "C" and "F," are bisymmetric with respect to a centerline 452R of right foot 20R. In one aspect, where a similar set of measurements is made at locations A'-H' on a left foot 20L, a location on each foot 20L and 20R, for example locations E and E', may be determined to be approximately bisymmetric.

FIG. 7A depicts an exemplary mat assembly 500 that incorporates a plurality of bioimpedance sensors 520, according to the present disclosure. Although sensors 520 are shown as toroidal sensors similar to sensors 90 depicted in FIG. 3A, sensors 520 may be any configuration of electrical measurement sensor, including the configurations shown in FIGS. 4, 5, and 6A-6B. Sensors 520 are distributed across substrate 510. In an aspect, a portion of substrate 510 is flexible. In one aspect, a portion of substrate 510 is rigid. In an aspect, electrodes of sensor 520 are electrically bare, thereby allowing conductive electrical contact with a patient's foot when a patient stands on mat assembly 500. In one aspect, electrodes of sensor 520 are electrically insulated, for example by an insulating cover layer (not shown in FIG. 7A), thereby allowing only capacitive electrical contact with a patient's foot when a patient stands on mat assembly 500.

In an aspect, mat assembly 500 comprises one of more temperature sensors (not shown in FIG. 7A), that detect the temperature of one or more locations on a foot. In one aspect, a temperature sensor is co-located with SEM sensor 520 so as to provide temperature and SEM measurements of a common location.

In one aspect of mat assembly 500, a signal is provided when the measured capacitance differs from a reference capacitance value by an amount greater than a first threshold and the measured temperature differs from a temperature reference value by an amount greater than a second threshold. In an aspect, one or both of the thresholds are predetermined. In one aspect, a first threshold is set at the corresponding reference capacitance value plus at least 5%, such as at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 150%, at least 200%, at least 250%, at least 300%, at least 400%, or at least 500%. In one aspect, a second threshold is set at the corresponding reference temperature value plus at least 5%, such as at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 150%, at least 200%, at least 250%, at least 300%, at least 400%, or at least 500%. In one aspect, one or both of the capacitance and temperature reference values are determined from prior measurements, for example a rolling average of the past 5 sequential measurements or by an average of multiple measurements made in an earlier time period, e.g. a month earlier.

In one aspect, one or both of the capacitance and temperature reference values are determined from measurements made when the tissue was in a known healthy state, for example while in a doctor's office when a clinician has made an examination of the tissue and determined that the tissue is healthy, i.e. not susceptible to the formation of a diabetic foot ulcer.

FIG. 7B depicts another exemplary mat assembly 502 that comprises arrays 530L and 530R of electrical sensors 520, where arrays 530L and 530R are disposed so as to underlie the left and right feet, respectively, of a patient while standing on mat assembly 502. In an aspect, outlines 540L and 540R of the left and right feet are drawn over arrays 530L and 530R so as to guide the patient to stand in the proper location.

FIG. 7C depicts an aspect of a mat assembly 504 that has one or more sensors 520 disposed within each of the outlines 540L and 540R. In an aspect, a sensors 520A is located in a position corresponding to portions of the foot that are most likely to develop an ulcer, for example the ball of a foot. In one aspect, sensors 520B may be located under the heel or other locations of a foot.

In one aspect, substrate 510 is partially transparent and mat 504 comprises a second substrate 512 on which are mounted one or more optical sensors 550. In an aspect, optical sensor 550 is a camera capable of imaging the underside of a foot of a patient standing on mat 504. In one aspect, optical sensor 550 is sensitive to visible light. In an aspect, optical sensor 550 is sensitive to infrared light.

The use of mat assemblies 500, 502, 504 and the like on a regular basis by patients can serve to detect changes in the health of their feet. For example, a baseline will be established by measurement of electrical characteristics, such as capacitance, of each foot at the time of examination by a clinician who verifies that there is no ulcer or indication of damage that would lead to formation of an ulcer in a patient. The patient then places the mat 500, 502, 504 in a readily accessible location in their home, for example in front of the bathroom sink. On a regular basis, such as daily while brushing their teeth, the patient triggers a measurement of their feet by the sensors 520. If the patient is standing on the same location, for example being guided by outlines 540L and 540R, then each sensor 520 and 550 is measuring the same position for each repeated measurement. In an aspect, a temperature measurement is made by an infrared sensor 550 or one of more temperature sensors (not shown in FIG. 7C) in mat assembly 500, 502, 504. In one aspect, an image is captured by an optical sensor 550 in mat assembly 504. This information is stored in a local memory or transmitted to a remote storage location, such as the doctor's office. Each daily measurement is compared to reference derived from previous measurements, for example a measurement made in a clinician's office or an average of last week's measurements. If the most recent measurement deviates from the reference, the patient is informed of the deviation. The patient can then consult a clinician for further evaluation and possible intervention. In an aspect, a change in the measured SEM value larger than the threshold triggers a notification. In one aspect, a change in the measured SEM value larger than a first threshold and a change in the measured temperature larger than a second threshold together trigger a notification. In an aspect, either a change in the measured SEM value larger than a first threshold or a change in the measured temperature larger than a second threshold triggers a notification. In one aspect, a first threshold is set at the corresponding reference SEM value plus at least 5%, such as at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 150%, at least 200%, at least 250%, at least 300%, at least 400%, or at least 500%. In one aspect, a second threshold is set at the corresponding reference temperature value plus at least 5%, such as at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 150%, at least 200%, at least 250%, at least 300%, at least 400%, or at least 500%. In an aspect, information such as an image of the underside of a patient's foot is always sent to a clinician for review.

In an aspect, measurements of the left and right foot are compared to each other. For example, with reference to FIGS. 6F and 6G, locations E and E' are compared to each other. In one aspect, a difference between the left and right measurements is compared to a reference and the patient notified if the difference exceeds a threshold.

Figure 8B:
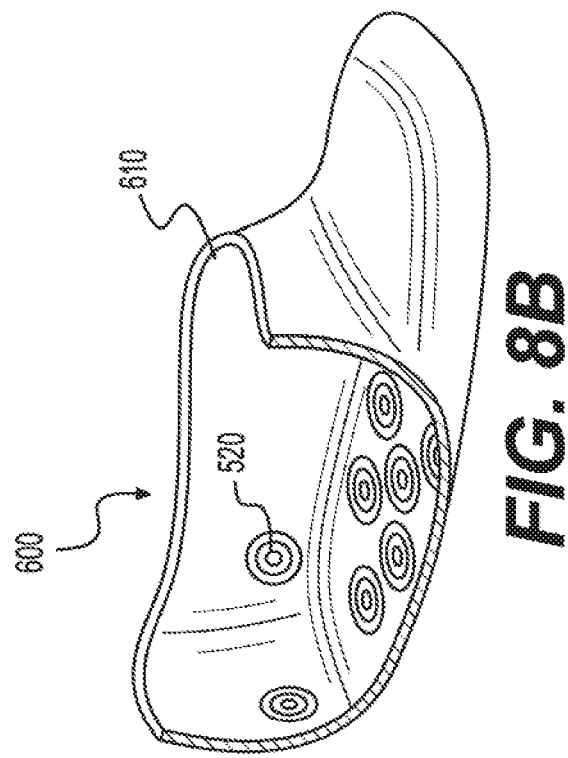
FIG. 8B is a cutaway view of the foot cover of FIG. 8A, showing the location of the bioimpedance sensors according to the present disclosure.
Figure 8A:
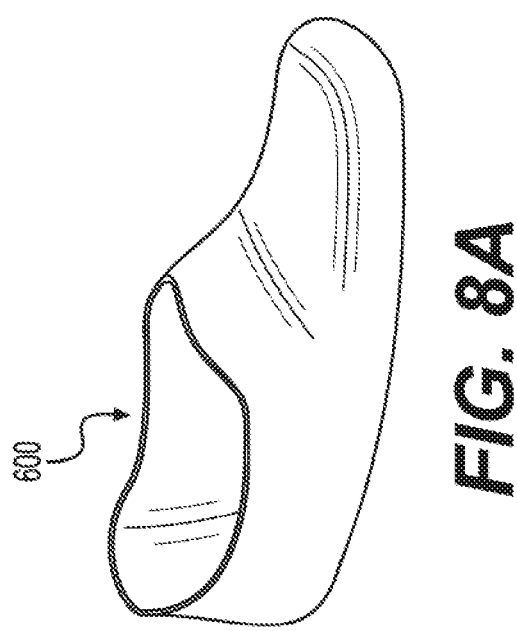
FIG. 8A discloses a foot cover that incorporates bioimpedance sensors according to the present disclosure.

FIG. 8A discloses a foot cover 600 that incorporates bioimpedance sensors 520 as shown in the cut-away view of FIG. 8B, according to the present disclosure. In an aspect, foot cover 600 comprises a sock or other flexible, conforming garment 610 into which a foot can be inserted. In one aspect, a flexible, conforming garment 610 may be a flexible shoe, similar to a "water shoe," made from a flexible, elastic material such as rubber. In an aspect, a flexible, conforming garment 610 may be a conventional shoe, for example a leather dress shoe or a sneaker. Sensors 520 are located in one or more locations that correspond to areas of concern for development of ulcers. In one aspect, sensors 520 are located under or around the heel of a flexible, conforming garment 610. In an aspect, sensors 520 are located on the sole of a flexible, conforming garment 610. In one aspect, sensors 520 are located in the area around the toes (not visible in FIG. 8B) of a flexible, conforming garment 610.

Figure 9:
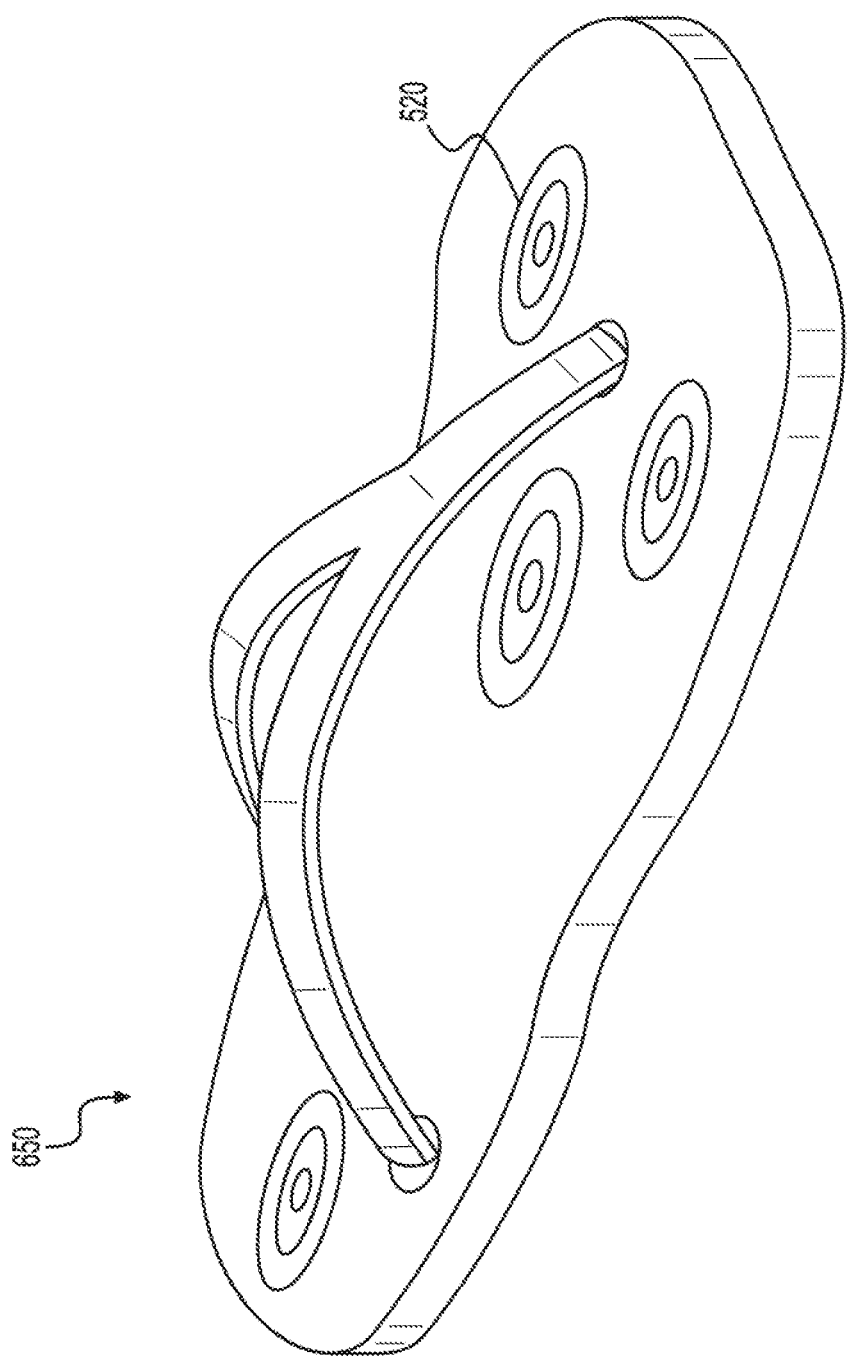
FIG. 9 disclose a sandal that incorporates bioimpedance sensors according to the present disclosure.

FIG. 9 discloses a sandal 650 that incorporates bioimpedance sensors 520, according to the present disclosure. One or more sensors 520 are disposed on a sandal in locations that correspond to areas of potential ulcer development.

Figure 10C:
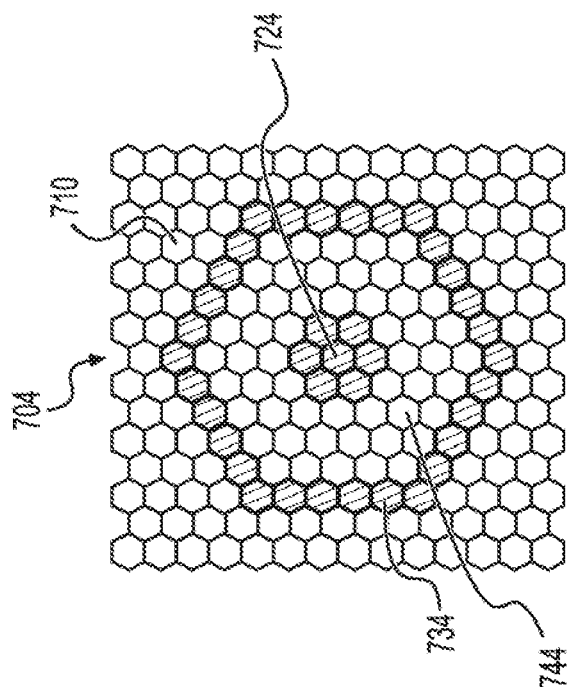
FIG. 10C depicts a third example configuration of the addressable electrodes of FIG. 5 that vary the performance capabilities of the sensor according to the present disclosure.
Figure 10B:
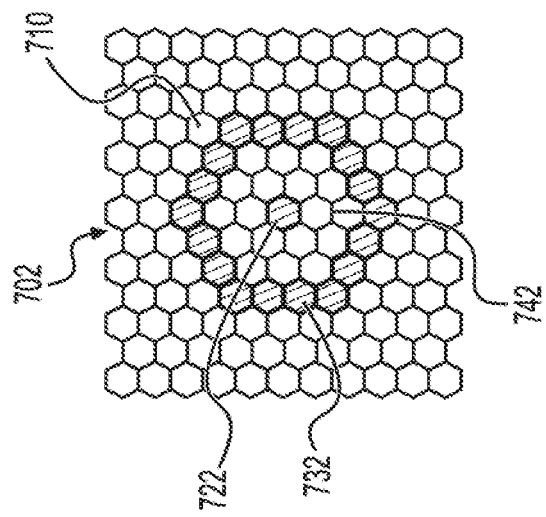
FIG. 10B depicts a second example configuration of the addressable electrodes of FIG. 5 that vary the performance capabilities of the sensor according to the present disclosure.
Figure 10A:
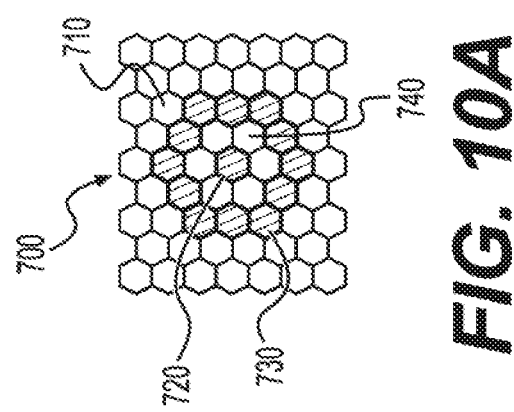
FIG. 10A depicts a first example configuration of the addressable electrodes of FIG. 5 that vary the performance capabilities of the sensor according to the present disclosure.

FIGS. 10A, 10B, and 10C depict configurations of addressable electrodes of FIG. 5 that vary the performance capabilities of a sensor, according to the present disclosure. FIG. 10A depicts an exemplary first configuration 700, where electrodes 710 are connected so as to form a center electrode 720 and a ring electrode 730, similar to electrodes of FIGS. 6A and 6B. Sensor configuration 700 has a gap 740 of a single row of electrodes 710, which results in a first field depth 150, with reference to FIG. 3B.

FIG. 10B depicts a second exemplary configuration 702 of the same array of sensors 710, where one electrode is connected to form a center electrode 722 while a plurality of electrodes 710 are connected to form a ring electrode 732 that is larger in diameter than ring electrode 730 and having a gap 742 that is larger than gap 740. Sensor configuration 702 will have a second field depth 150 that is larger than that of sensor configuration 700.

FIG. 10C depicts a third exemplary configuration 704 of the same array of sensors 710, where one electrode is connected to form a center electrode 724 while a plurality of electrodes 710 are connected to form a ring electrode 734 that is larger in diameter than ring electrodes 730 and 732 and having a gap 744 that is larger than gaps 740 and 742. Sensor configuration 704 will have a third field depth 150 that is larger than either of sensor configurations 700 or 702.

In an aspect, a mat assembly 500 comprises an array of electrodes 710 distributed across a portion of substrate 510. At a location of an array that corresponds to an area of concern on a patient's foot, mat assembly 500 is configured to form a sensor configuration 700 and make a first measurement, then reconfigure electrodes 710 to form a sensor configuration 702 and make a second measurement. The first and second measurements provide information about the difference in ECF at different depths below the skin of a foot, thereby providing improved knowledge of the tissue condition within the foot. In one aspect, mat assembly 500 is configured to then form a sensor configuration 704 and take a third measurement. Comparison of the three measurements provides even greater resolution of the internal tissue condition.

FIGS. 11A and 11B depict an exemplary aspect of a sensor assembly 500 configured to be placed in a known position on a patient's skin, according to the present disclosure. In this example, sensor assembly 500 has a shaped substrate 510 that is configured to conform to posterior and bottom surfaces of the heel of a foot 20. In one aspect, shaped substrate 510 is suitable for use with both a left foot 20L and a right foot 20R. Sensor assembly 500 comprises one or more sensors 520 disposed on the inner surface of shaped substrate 510. In this example, sensors 520 are configured as toroidal sensors as shown in FIG. 1A. In an aspect, the inner surface of shaped substrate 510 is lined with an array 400 of electrodes 410, with reference to FIG. 5, such that virtual sensors may be formed at any location. In one aspect, sensors of other shapes and configurations are provided on the inner surface of shaped substrate 510. In an aspect, shaped substrate 510 is a flexible panel (not shown in FIG. 11A) that can be conformed to a patient's skin, for example wrapped around the back of an ankle. In one aspect, sensor assembly 500 comprises a cable 530 to connect sensors 520 to one or more of a power source, a circuit configured to measure one or more of capacitance or other electrical property, a processor, a communication subsystem, or other type of electronic assembly (not shown in FIG. 11A).

FIG. 11B depicts an exemplary configuration of sensor assembly 500 where multiple sensors 520 disposed on shaped substrate 510 such that, for example when sensor assembly 500 is placed against the skin of a patient around the back, sides, and bottom of the right heel center. This enables multiple SEM measurements to be taken in repeatable location on the heel with sensor assembly 500 in a single position. In one aspect (not shown in FIGS. 11A and 11B), sensor assembly 500 is configured to be placed on a portion of the back of a patient thus providing the capability to make measurements at bisymmetric locations on the back. In an aspect, shaped substrate 510 is configured to match anatomical features of the target area of a patient. In one aspect, shaped substrate 510 comprises markings or other indicators that can be aligned with features of a patient's body, so as to enable measurements to be taken at the same location at time intervals over a period of time in the general range of hours to weeks. In one aspect, sensor assembly 500 is integrated into a lining of a garment or shoe or other article of clothing. In an aspect, sensor assembly 500 is integrated into a sheet, blanket, liner, or other type of bed clothing. In one aspect, sensor assembly 500 comprises a wireless communication capability, for example a passive radio frequency identification (RFID) or an inductive coupling, to allow actuation of sensors 520 without physically connecting to sensor assembly 500.

In an aspect, sensors 520 are coupled to electronics (not shown in FIG. 11B) that are configured to compare a current set of measurements to each other and to past measurements made in the same location. In an aspect, electronics of the present disclosure may provide a signal if one or more of certain conditions are met. Such conditions may include, but are not limited to, a change in the difference between measurements made at two locations when compared to the difference in measurements made at the same two locations at a previous time, and a change in the measured value at a particular location from prior measurements at the same location that is greater than a threshold amount.

Figure 12:
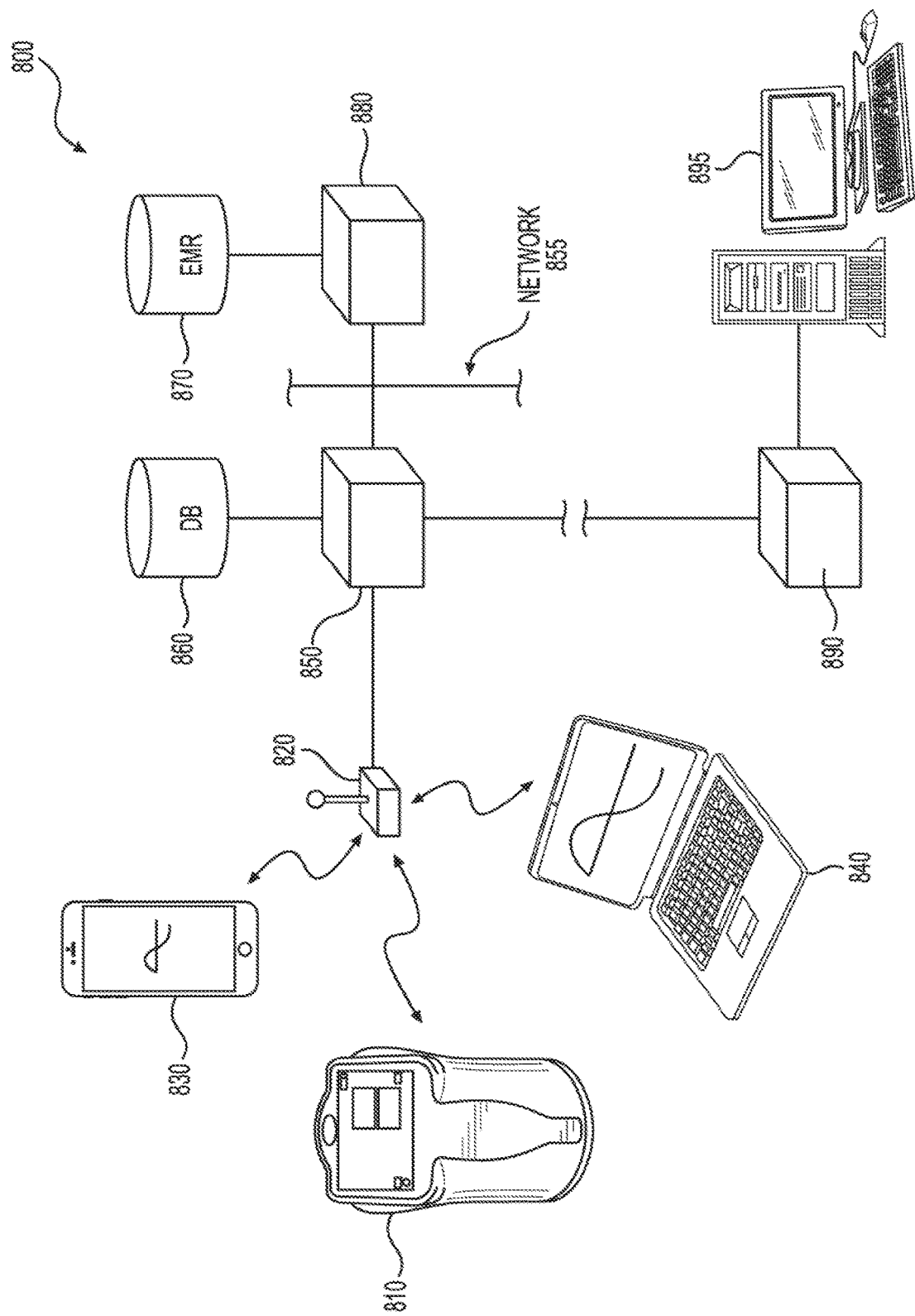
FIG. 12 depicts a schematic depiction of an integrated system for measurement, evaluation, storage, and transfer of SEM values according to the present disclosure.

FIG. 12 depicts a schematic depiction of an integrated system 800 for measurement, evaluation, storage, and transfer of SEM values, according to the present disclosure. In this example, system 800 comprises a SEM measurement apparatus 810, for example a SEM scanner 170, that comprises the capability to wirelessly communicate with a WiFi access point 820. Apparatus 810 communicates with one or more of a SEM application running on a server 850, an application running on a laptop computer 840, a "smart phone" 830, or other digital device. In an aspect, laptop computer 840 and smart phone 830 are carried by the user of apparatus 810, for example a nurse, and the application provides feedback and information to the user. In an aspect, information received from apparatus 180 for a patient is stored in a database 850. In one aspect, information received from apparatus 810 for a patient is stored in a database 860. In an aspect, information received from apparatus 810 is transferred over a network 855 to another server 880 that stores a portion of the information in an electronic medical record (EMR) 870 of the patient. In one aspect, information from apparatus 810 or retrieved from database 860 or EMR 870 is transferred to an external server 890 and then to a computer 895, for example a computer at the office of a doctor who is proving care for the patient.

In an aspect, apparatus 810 is one of a mat assembly 500, a foot cover 600, or other measurement device and one or both of smart phone 830 and laptop 840 are used by the patient to receive information and notifications related to measurements made by mat assembly 500.

Figure 13:
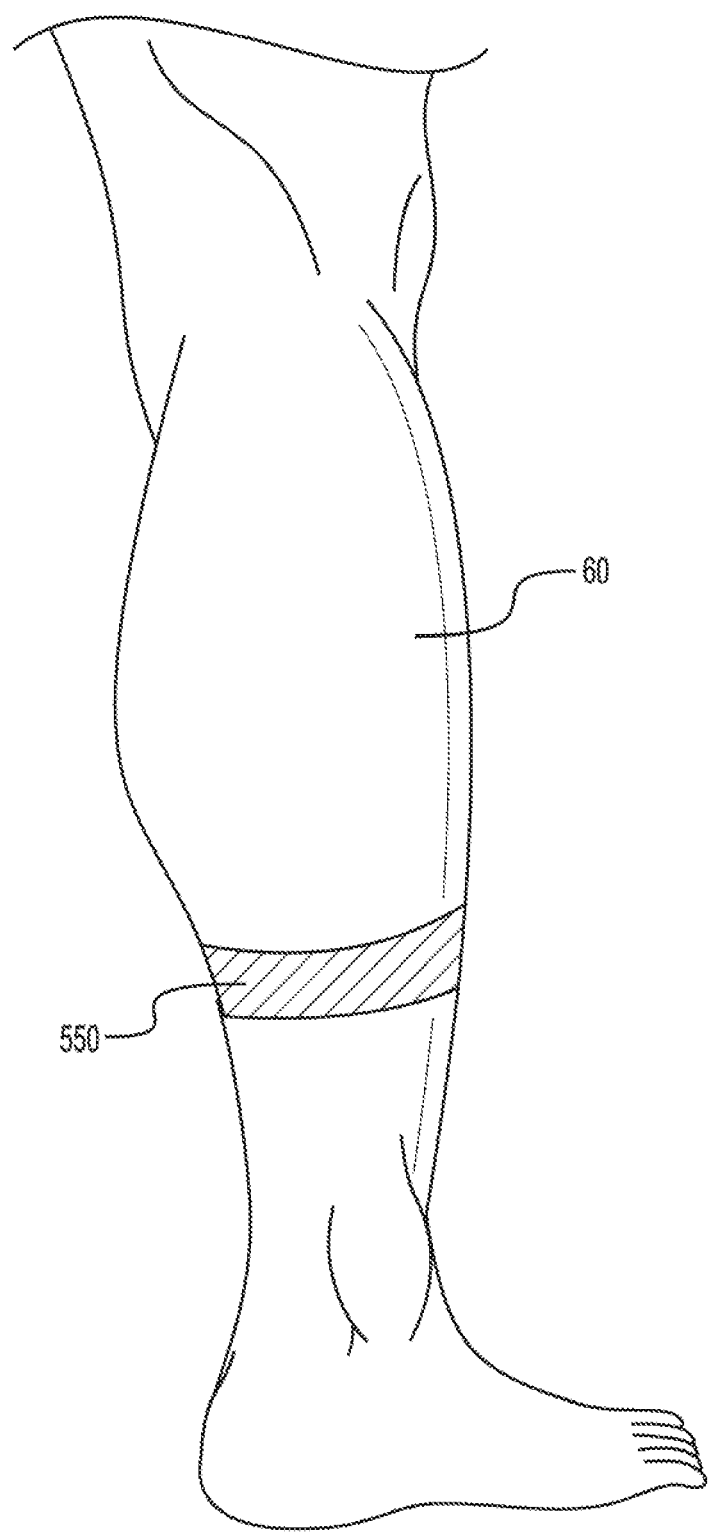
FIG. 13 depicts a sensing band according to the present disclosure.

FIG. 13 depicts a sensing band 550, according to the present disclosure. In one aspect, a SEM sensor as described herein, for example sensor 90 or sensor 400, is embedded in a band 554 that can be wrapped around a calf 60 as shown in FIG. 13. In an aspect, band 554 comprises sensors configured to measure one or more of oxygenation of the tissue, which may comprise measurement of one or both of oxyhemoglobin and deoxyhemoglobin, temperature of one or more points on the skin, pulse rate, blood volume and blood pressure. In one aspect, the combination of measurements made by band 554 provides information regarding the flow of blood to the foot, where reduced blood flow is a possible indication of susceptibility to formation of DFUs. In an aspect, this information comprises measurement of blood volume and refill times on the portion of the calf 60 that is proximate to band 554.

Figure 14B:
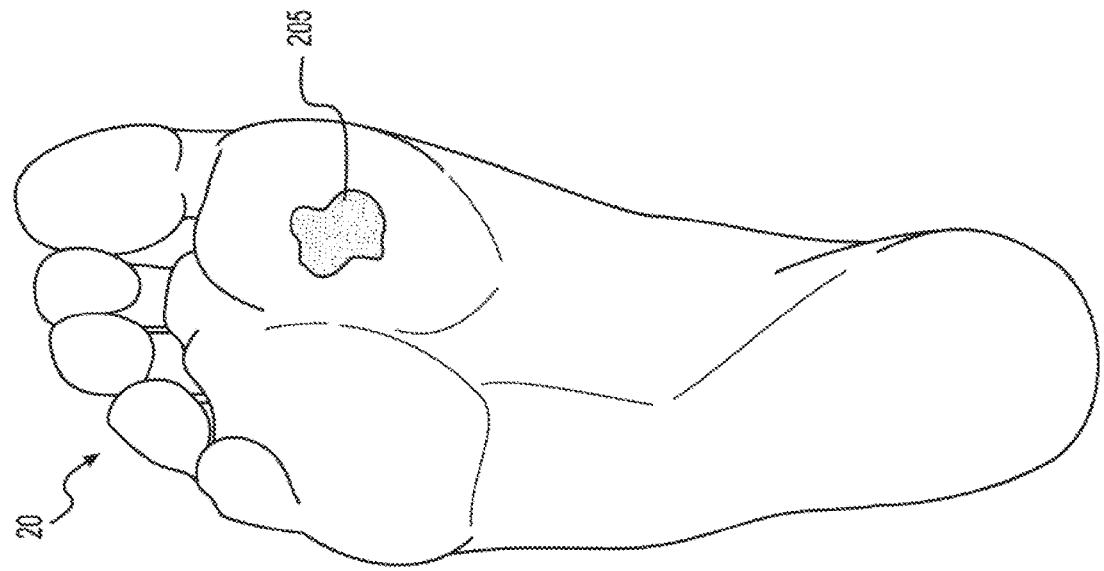
Figure 14A:
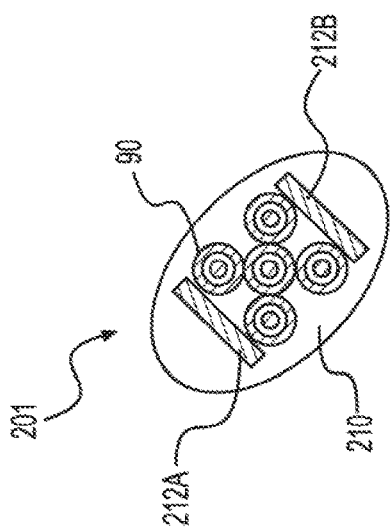

FIG. 14A depicts an integrated sensor and stimulator assembly 201 suitable for treatment of a pressure ulcer, according to the present disclosure. In an aspect, an integrated sensor and stimulator assembly 201 is provided to a patient in need thereof. Assembly 201 has a substrate 210 with a plurality of sensors 90 disposed on a first surface. Sensors 90 are configured to measure sub-epidermal moisture (SEM) as an indication of tissue health at the location of the respective sensor 90. In an aspect, there are two electrodes 212A and 212B that are in conductive contact with the skin of a patient (not shown in FIG. 14A) when the assembly 201 is placed on the skin. These electrodes 212A, 212B are connected to an external controller (not shown in FIG. 14A) that is configured to apply a therapeutic electrical stimulus to the tissue between the electrodes 212A, 212B, with the stimulus applied for periods having a time duration and a time interval between the periods. In an aspect, low level voltage and/or currents may enhance the healing of a pressure ulcer. Sensors 90 are individually connected to an external controller (not shown in FIG. 14A) that is configured to measure the capacitance of the respective sensors 90. In an aspect, the capacitance is measured in a time interval between the stimulus periods. In one aspect, a time interval can be in the general range of hours to weeks. In an aspect, assembly 201 comprises an absorbent pad and a non-stick layer (not shown in FIG. 14A) overlaid upon sensors 90 and electrodes 212A, 212B. In an aspect, assembly 201 comprises a layer of adhesive (not shown in FIG. 14A) overlaid upon a portion of substrate 210 so as to allow assembly 201 to be adhesively attached to the skin of a patient. In an aspect, substrate 201 may be permeable to gas while impervious to fluid.

The combination of a standard bandage (the absorbent pad, non-stick layer, and covering substrate) with a therapeutic instrument, such as electrodes 212A, 212B and the associated external controller, with one or more sensors 90 provides a means of protecting the wound, improving the healing process, and monitoring the healing without disturbing the assembly 201.

FIG. 14B depicts the sole of a foot 20 of a patient having a pressure ulcer 205.

FIG. 14C depicts an assembly 201 adhered to the sole of foot 20 over the pressure ulcer 205. In an aspect, assembly 201 is placed over ulcer 205 and left in place for several days. In an aspect, assembly 201 comprises a toroidal pad that relieves the pressure on the pressure ulcer 205. The external controller of electrodes 212A, 212B is periodically attached to electrodes 212A, 212B to apply a therapeutic stimulus. During the interval between these stimuli, the external controller of the sensors 90 is attached to one or more of the sensors 90 to make a SEM measurement.

In an aspect, assembly 201 comprises a battery and wireless communication capability that enables the external controller to cause the stimulus to be applied through electrodes 212A, 212B without a wired connection to the assembly. Similarly, the assembly may be configured to allow the external controller to communicate with the sensors 90 to make and receive SEM measurements without a wired connection. In an aspect, the assembly 201 comprises a microcontroller configured to apply the therapeutic stimulus and make SEM measurements and wirelessly transmit information, such as the SEM values.

It will be apparent to those of ordinary skill in the art that the concept of combining therapeutic instruments and SEM sensors can be applied to other types of wounds and to other locations on the body besides the sole of the foot, such as an ankle, or a bony prominence.

FIG. 14D depicts a bandage assembly 202 adapted for placement over a pressure ulcer on the sacrum of a patient in need thereof. The assembly 202 comprises substrate 220 that is porous to gas while impervious to fluid. The assembly 202 comprises a pad 222 (seen from the external side in FIG. 14D) that provides both protective padding and absorption. In this example, a single sensor 90 is positioned on the underside of the pad 222 such that the sensor is directly over the pressure ulcer when the assembly is applied over an early-stage pressure ulcer with unbroken skin. The electrodes 214A, 214B are location adjacent to the sensor 90 and on the same underside so that they will be in contact with the skin of the patient. In this configuration, the assembly 202 can be placed over an early-stage ulcer and protect, improve the healing process, and monitor the progress of the healing with removal of the assembly 202 or disturbance of the wound.

Having now generally described the invention, the same will be more readily understood through reference to the following examples that are provided by way of illustration, and are not intended to be limiting of the present disclosure, unless specified.

EXAMPLES

Example 1: Taking SEM Measurements at Multiple Locations of the Foot

SEM measurements were taken at the foot using one of three methods below to ensure complete contact of an electrode with the skin of a human patient.

Figure 15A:
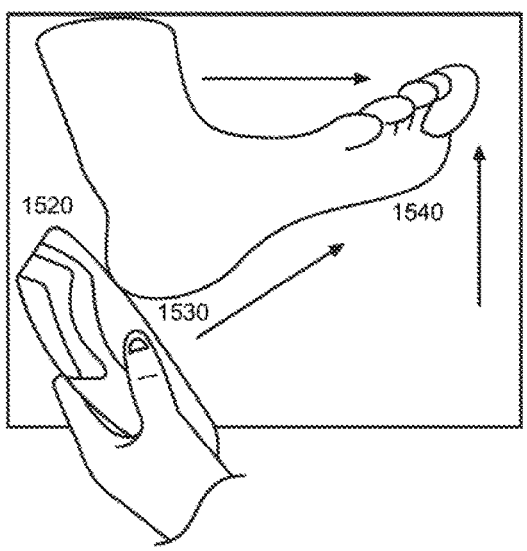
FIG. 15A illustrates an exemplary method for taking SEM measurements starting at the posterior heel in accordance with the present disclosure.

FIG. 15A illustrates a method used to take SEM measurements starting at the posterior heel using an apparatus according to the present disclosure. First, the forefoot was dorsiflexed such that the toes were pointing towards the shin. Second, a bioimpedance sensor 1520 was positioned at the base of the heel 1530. The electrode was adjusted for full contact with the heel, and multiple SEM measurements were then taken in a straight line towards the toes, including the ball of the foot 1540. The ball of the foot is one of the primary locations of diabetic foot ulcer.

Figure 15B:
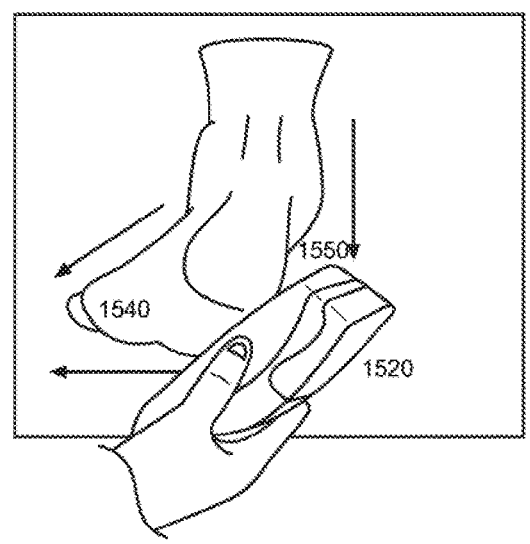
FIG. 15B illustrates an exemplary method for taking SEM measurements starting at the lateral heel in accordance with the present disclosure.

FIG. 15B illustrates a method used to take SEM measurements starting at the lateral heel using an apparatus according to the present disclosure. First, the toes were pointed away from the body and rotated inward towards the medial side of the body. Second, an electrode was placed on the lateral side of the heel 1550. A bioimpedance sensor 1520 was adjusted for full contact with the heel, and multiple SEM measurements were taken in a straight line towards the bottom of the foot. The ball of the foot 1540 is also shown in FIG. 15B.

Figure 15C:
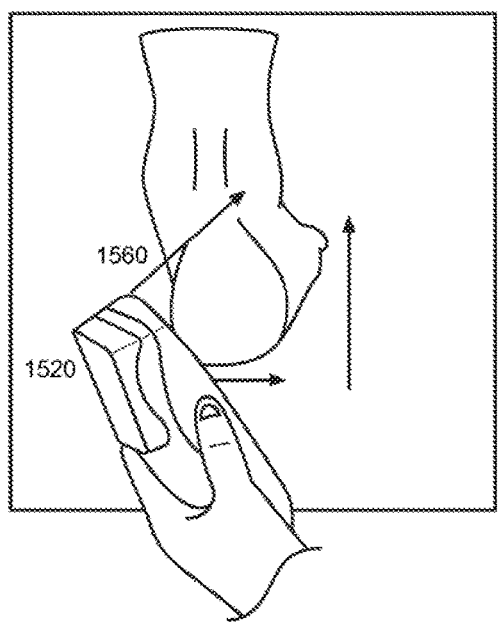
FIG. 15C illustrates an exemplary method for taking SEM measurements starting at the medial heel in accordance with the present disclosure.

FIG. 15C illustrates a method used to take SEM measurements starting at the medial heel using an apparatus according to the present disclosure. First, the toes were pointed away from the body and rotated outwards toward the lateral side of the body. Second, the electrode was placed on the medial side of the heel 1560. A bioimpedance sensor 1520 was adjusted for full contact with the heel, and multiple measurements were taken around the back of the heel in a curve.

From the foregoing, it will be appreciated that the present invention can be embodied in various ways, which include but are not limited to the following:

Embodiment 1

An apparatus for assessing susceptibility of tissue to formation of a diabetic foot ulcer, the apparatus comprising: a plurality of electrodes embedded on a substrate, where a pair of the electrodes is capable of forming a capacitive sensor configured to measure a first capacitance of a first region of tissue proximate to the capacitive sensor, a drive circuit electronically coupled to the electrodes, a processor electronically coupled to the drive circuit, and a non-transitory computer-readable medium electronically coupled to the processor and comprising instructions stored thereon that, when executed on the processor, perform the steps of: receiving information regarding the measured first capacitance from the drive circuit, comparing the measured first capacitance to a first reference value, and providing a signal if the measured first capacitance differs from the first reference value by an amount greater than a first predetermined threshold.

Embodiment 2

The apparatus of embodiment 1, where the first reference value is predetermined.

Embodiment 3

The apparatus of embodiment 1, where the first reference value is determined by measurement of the first capacitance at a time when the first region of tissue is healthy.

Embodiment 4

The apparatus of embodiment 1, where the first reference value is determined from measurements of the first capacitance at the first region of tissue one or more times prior to the most recent measurement of the first capacitance.

Embodiment 5

The apparatus of embodiment 1, where the first reference value is determined by a measurement from a bisymmetric location.

Embodiment 6

The apparatus of embodiment 1, where the first reference value is a measurement of a second capacitance of a second region of tissue that is separated from the first region of tissue.

Embodiment 7

The apparatus of embodiment 6, where the second region of tissue is known to be healthy.

Embodiment 8

The apparatus of embodiment 6, where the second capacitance is measured at approximately the same time as the first capacitance.

Embodiment 9

The apparatus of embodiment 1, the apparatus further comprising one or more temperature sensors that are configured to measure a temperature of the first region of tissue and are coupled to the processor, where: the instructions further comprise: a step of receiving information regarding the measured temperature from the one or more temperature sensors, and a step of comparing the measured temperature to a second reference value, and a step of providing a signal comprising providing the signal if the measured first capacitance differs from the first reference value by an amount greater than the predetermined first threshold and the measured temperature differs from the second reference value by an amount greater than a predetermined second threshold.

Embodiment 10

The apparatus of embodiment 1, the apparatus further comprising one or more optical sensors configured to image an underside of a foot of a patient while the patient is standing on the substrate.

Embodiment 11

A method for assessing susceptibility of tissue to formation of a diabetic foot ulcer, the method comprising: obtaining a first capacitance value at a first location of a patient's skin; obtaining a temperature measurement at the first location of a patient's skin; and determining that the first location of a patient's skin is susceptible to formation of a diabetic foot ulcer when the first capacitance value differs from a first reference value by an amount greater than a first predetermined threshold and the temperature measurement differs from a second reference value by an amount greater than a second predetermined threshold.

Embodiment 12

The method of embodiment 11, where the first reference value is predetermined.

Embodiment 13

The method of embodiment 11, where the first reference value is determined by measurement of the first capacitance at a time when the first location of a patient's skin is healthy.

Embodiment 14

The method of embodiment 11, where the first reference value is determined from measurements of the first capacitance at the first location of a patient's skin at one or more times prior to the most recent measurement of the first capacitance.

Embodiment 15

The method of embodiment 11, where the first reference value is a measurement of a second capacitance of a second location of a patient's skin that is separated from the first location of a patient's skin.

Embodiment 16

The method of embodiment 15, where the second region of a patient's skin is known to be healthy.

Embodiment 17

The method of embodiment 15, where the second capacitance is measured at approximately the same time as the first capacitance.

Embodiment 18

A method for assessing susceptibility of tissue to formation of a diabetic foot ulcer, the method comprising: obtaining a first sub-epidermal moisture (SEM) value at a first location of a patient's skin; obtaining a temperature measurement at the first location of a patient's skin; and determining that the first location of a patient's skin is susceptible to formation of a diabetic foot ulcer when the first SEM value differs from a first reference value by an amount greater than a first predetermined threshold and the temperature measurement differs from a second reference value by an amount greater than a second predetermined threshold.

Embodiment 19

The method of embodiment 18, where the first reference value is predetermined.

Embodiment 20

The method of embodiment 18, where the first reference value is determined by measurement of the first SEM value at a time when the first location of a patient's skin is healthy.

Embodiment 21

The method of embodiment 18, where the first reference value is determined from measurements of the first SEM value at the first location of a patient's skin at one or more times prior to the most recent measurement of the first SEM value.

Embodiment 22

The method of embodiment 18, where the first reference value is a measurement of a second SEM value of a second location of a patient's skin that is separated from the first location of a patient's skin.

Embodiment 23

The method of embodiment 22, where the second location of a patient's skin is known to be healthy.

Embodiment 24

The method of embodiment 22, where the second SEM value is measured at approximately the same time as the first SEM value.

Embodiment 25

An integrated apparatus for treating a diabetic foot ulcer in a patient in need thereof, the apparatus comprising: a plurality of sensors disposed on a flexible substrate, where the plurality of sensors are configured to measure sub-epidermal moisture (SEM) values at respective locations of the patient's skin; two electrodes disposed on the flexible substrate; and an external controller electrically connected to the two electrodes, where the external controller controls the two electrodes to detect conductive contact with the patient's skin during a SEM measurement period, and the external controller controls the two electrodes to apply a therapeutic stimulus to the patient during a therapeutic phase.

Embodiment 26

The apparatus of embodiment 25, further comprising an absorbent pad.

Embodiment 27

The apparatus of embodiment 25, further comprising a layer of adhesive.

Embodiment 28

The apparatus of embodiment 25, where the flexible substrate is permeable to gas while impervious to fluid.

Embodiment 29

An integrated apparatus for treating a diabetic foot ulcer in a patient in need thereof, the apparatus comprising: a sensor comprising two electrodes disposed on a flexible substrate such that a current passing between the electrodes will pass through tissue proximate to a location of the patient's skin; and an external controller electrically connected to the two electrodes.

Embodiment 30

The integrated apparatus of embodiment 29, where the external controller controls the two electrodes to detect conductive contact with the patient's skin during a SEM measurement period, and the external controller controls the two electrodes to apply a therapeutic stimulus to the patient during a therapeutic phase.

While the invention has been described with reference to particular aspects, it will be understood by those skilled in the art that various changes may be made and equivalents may be substituted for elements thereof without departing from the scope of the invention. In addition, many modifications may be made to a particular situation or material to the teachings of the invention without departing from the scope of the invention. Therefore, it is intended that the invention not be limited to the particular aspects disclosed but that the invention will include all aspects falling within the scope and spirit of the appended claims.

We claim:

1. A method for assessing susceptibility of foot tissue to formation of a diabetic foot ulcer, said method comprising:
   obtaining a first sub-epidermal moisture (SEM) value at a first foot location of a patient using an apparatus comprising a plurality of sensors, wherein said plurality of sensors are configured to measure SEM values at respective locations of said patient's foot;
   obtaining a temperature measurement at said first foot location of said patient; and
   determining that said first foot location of said patient is susceptible to formation of a diabetic foot ulcer when said first SEM value differs from a first reference value by an amount greater than a first predetermined threshold and said temperature measurement differs from a second reference value by an amount greater than a second predetermined threshold.

2. The method of claim 1, wherein said first reference value is predetermined.

3. The method of claim 1, wherein said first reference value is determined by measurement of said first SEM value at a time when said first foot location of said patient is healthy.

4. The method of claim 1, wherein said first reference value is determined from measurements of said first SEM value at said first foot location of said patient at one or more times prior to the most recent measurement of said first SEM value.

5. The method of claim 1, wherein said first reference value is a measurement of a second SEM value of a second foot location of said patient that is separated from said first foot location of a said patient.

6. The method of claim 5, wherein said second foot location of said patient is selected from the group consisting of a pad of one of said patient's feet and a heel of one of said patient's feet.

7. The method of claim 5, wherein said foot second location of said patient is a ball of one of said patient's feet.

8. The method of claim 5, wherein said first and second foot locations of said patient are located on one of said patient's feet.

9. The method of claim 5, wherein said first and second foot locations of said patient are located on different feet of said patient.

10. The method of claim 5, wherein said second foot location of said patient is known to be healthy.

11. The method of claim 5, wherein said second SEM value is measured at approximately the same time as said first SEM value.

12. The method of claim 1, further comprising treating said first foot location of said patient determined to be susceptible to formation of a diabetic foot ulcer by applying a therapeutic electrical stimulus to said first foot location of said patient, wherein said stimulus is applied for periods having a time duration and a time interval between the periods.

13. The method of claim 12, wherein the time interval is in the range of hours.

14. The method of claim 12, wherein the time interval is in the range of weeks.

15. The method of claim 12, wherein the therapeutic electrical stimulus is a low level voltage.

16. The method of claim 12, wherein the therapeutic electrical stimulus is a low level current.

17. The method of claim 1, wherein said first foot location of said patient is selected from the group consisting of a pad of one of said patient's feet and a heel of one of said patient's feet.

18. The method of claim 1, wherein said first foot location of said patient is a ball of one of said patient's feet.

* * * * *